US005449756A

United States Patent [19]
Taniguchi et al.

[11] Patent Number: 5,449,756
[45] Date of Patent: Sep. 12, 1995

[54] RECOMBINANT PROTEIN RECEPTOR FOR IL-2

[75] Inventors: Tadatsugu Taniguchi, Ibaraki; Masanori Hatakeyama, Suita; Sejiro Minamoto, Minou; Takeshi Kono, Ikeda; Takeshi Doi, Kodaira; Masayuki Miyasaka, Urawa; Mitsuru Tsudo; Hajime Karasuyama, both of Tokyo, all of Japan

[73] Assignee: Boehringer Ingelheim International GmbH, Germany

[21] Appl. No.: 88,592

[22] Filed: Jul. 9, 1993

Related U.S. Application Data

[60] Continuation of Ser. No. 865,155, Apr. 8, 1992, abandoned, which is a division of Ser. No. 487,059, Mar. 5, 1990, Pat. No. 5,198,359.

[30] Foreign Application Priority Data

Mar. 7, 1989 [EP]  European Pat. Off. ............ 89104023
May 29, 1989 [EP]  European Pat. Off. ............ 89109656
Jul. 20, 1989 [EP]  European Pat. Off. ............ 89113310

[51] Int. Cl.$^6$ ............................................ C07K 14/715
[52] U.S. Cl. ........................................ 530/350; 435/69.1; 536/23.5
[58] Field of Search ...................... 435/69.1, 172.2; 530/350, 387

[56] References Cited

FOREIGN PATENT DOCUMENTS

0162699A2  11/1985  European Pat. Off.
0202975A2  11/1986  European Pat. Off.
WO89/00168  1/1989  WIPO.
8900168  1/1989  WIPO ........................ C07K 15/00

OTHER PUBLICATIONS

R.N.A.S., 86:1982–86, Mar. 1989, Tsudo et al. Characterization of the interleukin-2 receptor β chain using three distinct monoclonal antibodies.
Cosman et al., Nature 312:768–771 (1984).
Dukovich et al., Nature 327:518–522 (1987).
Greene et al., J. Exp. Med. 162:363–368 (1985).
Gutierrez-Ramos et al., Eur. J. Immunol. 19:201–204 (1989).
Hatakeyama et al., J. Exp. Med. 166:362–275 (1987).
Hatakeyama et al., Nature 318:467–470 (1985).
Hatakeyama et al., Science 244:551–556 (1989).
Herrmann et al., Immunobiology 175:145–158 (1987).
Kondo et al., Nature 327:64–67 (1987).
Kruppa et al., Immunobiology 175:343–344 (1987).
Leonard et al., Nature 311:626–631 (1984).
Nikaido et al, Nature 311:631–635 (1984).
Robb et al., Proc. Natl. Acad. Sci. USA 84:2002–2006 (1987).
Robb et al., J. Exp. Med. 160:1126–1146 (1984).
Robb et al., J. Exp. Med. 165:1201–1206 (1987).
Seed, B. Nature 329:840–842 (1987).
Seed et al., Proc. Natl. Acad. Sci. USA 84:3365–3369 (1987).
Sharon et al., J. Exp. Med. 167:1265–1270 (1988).
Sharon et al., Science 234:859–863 (1986).
Sims et al., Science 241:585–589 (1988).
Smith et al., Science 238:1704–1707 (1987).
Teishigawara et al., J. Exp. Med. 165:223–238 (1987).
Treiger et al., J. Immunol. 136(11):4099–4105 (1986).
Tsudo et al., J. Immunol. 143(12):4039–4043 (1989).
Tsudo et al., Proc. Natl. Acad. Sci. USA 86:1982–1986 (1989).
Tsudo et al., Proc. Natl. Acad. Sci. USA 84:4215–4218 (1987).
Tsudo et al., Proc. Natl. Acad. Sci. 83:9694–9698 (1986).
Yodoi et al., J. Immunol. 134(1):1623–1630 (1985).

*Primary Examiner*—Garnette D. Draper
*Assistant Examiner*—John R. Ulm
*Attorney, Agent, or Firm*—Stern, Kessler, Goldstein & Fox

[57] ABSTRACT

The present invention is directed to recombinant the IL-21Rβ chain or fragments thereof, cDNA coding therefore, vectors containing said cDNA, hosts transfected by said vectors, and monoclonal antibodies to said recombinant IL-2Rβ or fragments thereof.

1 Claim, 23 Drawing Sheets

```
                                                        GCAGCCAGAGCTCAGCAGGGCCCTGGAGAGATGG                    34

CCACGGTCCCAGCACCGGGGAGGACTGGAGAGCGCGCTGCCACCGCCCC                                                       134

ATGTCTCAGCCAGGGCTTCCTCCTCGGCTCCACCCTGTGGATGTA ATG                                                        173
                                                  Met
                                                  -26

-25  GCG GCC CCT GCT CTG TCC TGG CGT CTG CCC CTC CTC ATC                                                      212
     Ala Ala Pro Ala Leu Ser Trp Arg Leu Pro Leu Leu Ile

-12  CTC CTG CCC CTG GCT ACC TCT TGG GCA TCT GCA GCG                                                          251
     Leu Leu Pro Leu Ala Thr Ser Trp Ala Ser Ala Ala

2   GTG AAT GGC ACT TCC CAG TTC AGA TGC TTC TAC AAC TCG                                                      290
     Val Asn Gly Thr Ser Gln Phe Arg Cys Phe Tyr Asn Ser

15   AGA GCC AAC ATC TCC TGT CTC TGG AGC CAA GAT GGG GCT                                                      329
     Arg Ala Asn Ile Ser Cys Val Trp Ser Gln Asp Gly Ala

28   CTG CAG GAC ACT TCC TGC TGC CAA GTC CAT GCC TGG CCG GAC                                                  368
     Leu Gln Asp Thr Ser Cys Cys Gln Val His Ala Trp Pro Asp

41   AGA CGG TGG AAC CAA ACC TGT GAG CTG CTC CCC GTG
     Arg Arg Trp Asn Gln Thr Cys Glu Leu Leu Pro Val
```

| # | | | | | | | | | | | | | | # |
|---|---|---|---|---|---|---|---|---|---|---|---|---|---|---|
| 54 | AGT Ser | CAA Gln | GCA Ala | TCC Ser | TGG Trp | GCC Ala | TGC Cys | AAC Asn | CTG Leu | ATC Ile | CTC Leu | GGA Gly | GCC Ala | 407 |
| 67 | CCA Pro | GAT Asp | TCT Ser | CAG Gln | AAA Lys | CTG Leu | ACC Thr | ACA Thr | GTT Val | GAC Asp | ATC Ile | GTC Val | ACC Thr | 446 |
| 80 | CTG Leu | AGG Arg | GTG Val | CTG Leu | TGC Cys | CGT Arg | GAG Glu | GGG Gly | GTG Val | CGA Arg | TGG Trp | AGG Arg | GTG Val | 485 |
| 93 | ATG Met | GCC Ala | ATC Ile | CAG Gln | GAC Asp | TTC Phe | AAG Lys | CCC Pro | TTT Phe | GAG Glu | AAC Asn | CTT Leu | CGC Arg | 524 |
| 106 | CTG Leu | ATG Met | GCC Ala | CCC Pro | ATC Ile | TCC Ser | CTC Leu | CAA Gln | GTT Val | GTC Val | CAC His | GTG Val | GAG Glu | 563 |
| 119 | ACC Thr | CAC His | AGA Arg | TGG Cys | AAC Asn | ATA Ile | AGC Ser | TGG Trp | GAA Glu | ATC Ile | TCC Ser | CAA Gln | GCC Ala | 602 |
| 132 | TCC Ser | CAC His | TAC Tyr | TTT Phe | GAA Glu | AGA Arg | CAC His | CTG Leu | GAG Glu | TTC Phe | GAG Glu | GCC Ala | CGG Arg | 641 |
| 145 | ACG Thr | CTG Leu | TCC Ser | CCA Pro | GGC Gly | CAC His | AGA Arg | ACC Thr | TGG Trp | GAG Glu | GAG Glu | GCC Ala | CTG Leu | 680 |

| | | | | | | | | | |
|---|---|---|---|---|---|---|---|---|---|
| 158 | CTG Leu | ACT Thr | CTC Leu | AAG Lys | CAG Gln | AAG Lys | CAG Gln | GAA Glu | TGG Trp | ATC Ile | TGC Cys | CTG Leu | GAG Glu | 719 |
| 171 | ACG Thr | CTC Leu | ACC Thr | CCA Pro | GAC Asp | ACC Thr | CAG Gln | TAT Tyr | GAG Glu | TTT Phe | CAG Gln | GTG Val | CGG Arg | 758 |
| 184 | GTC Val | AAG Lys | CCT Pro | CTG Leu | CAA Gln | GGC Gly | GAG Glu | TTC Phe | ACG Thr | ACC Thr | TGG Trp | AGC Ser | CCC Pro | 797 |
| 197 | TGG Trp | AGC Ser | CAG Gln | CCC Pro | CTG Leu | GCC Ala | TTC Phe | AGG Arg | ACA Thr | AAG Lys | CCT Pro | GCA Ala | GCC Ala | 836 |
| 210 | CTT Leu | GGG Gly | AAG Lys | GAC Asp | ACC Thr | ATT Ile | CCG Pro | TGG Trp | CTC Leu | GGC Gly | CAC His | CTC Leu | CTC Leu | 875 |
| 223 | GTG Val | GGC Gly | CTC Leu | AGC Ser | GGG Gly | GCT Ala | TTT Phe | GGC Gly | TTC Phe | ATC Ile | ATC Ile | TTA Leu | GTG Val | 914 |
| 236 | TAC Tyr | TTG Leu | CTG Leu | ATC Ile | AAC Asn | TGC Cys | AGG Arg | AAC Asn | ACC Thr | GGG Gly | CCA Pro | TGG Trp | CTG Leu | 953 |
| 249 | AAG Lys | AAG Lys | CTC Leu | CTG Leu | AAG Lys | TGT Cys | AAC Asn | ACC Thr | CCA Pro | GAC Asp | CCC Pro | TCG Ser | AAG Lys | 992 |
| 262 | TTC Phe | TTT Phe | TCC Ser | CAG Gln | CTG Leu | AGC Ser | TCA Ser | GAG Glu | CAT His | GGA Gly | GGA Gly | GAC Asp | GTC Val | 1031 |

FIG. 1B-3

| Pos | | | | | | | | | | | | | Num |
|---|---|---|---|---|---|---|---|---|---|---|---|---|---|
| 275 | CAG Gln | AAG Lys | TGG Trp | CTC Leu | TCT Ser | TCG Ser | CCC Pro | TTC Phe | CCC Pro | TGA Ser | TCC Ser | TTC Phe | 1070 |
| 288 | AGC Ser | CCT Pro | GGC Gly | GGC Gly | CTG Leu | GCA Ala | GAC Asp | CCT Pro | GAG Glu | TCG Ser | CCA Pro | CTA Leu | GAA Glu | 1109 |
| 301 | GTG Val | CTG Leu | GAG Glu | AGG Arg | GAC Asp | AAG Lys | GTG Val | ACG Thr | GAG Glu | CTG Leu | CCA Pro | CTG Leu | CAG Gln | 1148 |
| 314 | CAG Gln | GAC Asp | AAG Lys | GTG Val | CCT Pro | GAG Glu | CCC Pro | GCA Ala | TCC Ser | CTC Leu | CTG Leu | AAC Asn | 1187 |
| 327 | CAC His | TCG Ser | CTG Leu | ACC Thr | AGC Ser | TGC Cys | TTC Phe | ACC Thr | AAC Asn | TTA Leu | AGC Ser | AGC Ser | 1226 |
| 340 | TTC Phe | TTC Phe | CAC His | CTC Leu | CCG Pro | GAT Asp | GCC Ala | TTC Phe | ACC Thr | CAG Gln | TTG Leu | GAG Glu | ATA Ile | GAG Glu | GCC Ala | TGC Cys | 1265 |
| 353 | CAG Gln | GTG Val | TAC Tyr | TTT Phe | ACT Thr | TAC Tyr | GAC Asp | CCC Pro | GGG Gly | GCA Ala | TAC Tyr | TCA Ser | GAG Glu | GAA Glu | GAC Asp | 1304 |
| 366 | CCT Pro | GAT Asp | GAG Glu | GGT Gly | GTG Val | GCC Ala | GGT Gly | GCA Ala | CCC Pro | ACA Thr | GGG Gly | TCT Ser | TCC Ser | 1343 |
| 379 | CCC Pro | CAA Gln | CCC Pro | CTG Leu | CAG Gln | CCT Pro | CTG Leu | TCA Ser | GGG Gly | GAG Glu | GAC Asp | GCC Ala | 1382 |

FIG.1B-4

| | | | | | | | | | | | | |
|---|---|---|---|---|---|---|---|---|---|---|---|---|
| 392 | TAC Tyr | TGC Cys | ACC Thr | TTC Phe | CCC Pro | TCC Ser | AGG Arg | GAT Asp | GAC Asp | CTG Leu | CTG Leu | CTC Leu | TTC Phe | 1421 |
| 405 | TCC Ser | CCC Pro | AGT Ser | CTC Leu | CTC Leu | GGT Gly | GGC Gly | CCC Pro | CCC Pro | CCA Pro | AGC Ser | ACT Thr | 1460 |
| 418 | GCC Ala | CCT Pro | GGG Gly | GGC Gly | AGT Ser | GGG Gly | GCC Ala | GGT Gly | GAA Glu | GAG Glu | AGG Arg | ATG Met | CCC Pro | 1499 |
| 431 | CCT Pro | TCT Ser | TTG Leu | CAA Gln | GAA Glu | AGA Arg | GTC Val | CCC Pro | AGA Arg | GAC Asp | TGG Trp | GAC Asp | CCC Pro | 1538 |
| 444 | CAG Gln | CCC Pro | CTG Leu | GGG Gly | CCT Pro | CCA Pro | ACC Thr | CCA Pro | GGA Gly | GTC Val | CCA Pro | GAC Asp | CTG Leu | 1577 |
| 457 | GTG Val | GAT Asp | TTT Phe | CAG Gln | CCA Pro | CCC Pro | CCT Pro | GAG Glu | CTG Leu | GTG Val | CTG Leu | CGA Arg | GAG Glu | 1616 |
| 470 | GCT Ala | GGG Gly | GAG Glu | GAG Glu | GTC Val | CCT Pro | GAC Asp | GCT Ala | GGC Gly | CCC Pro | AGG Arg | GAG Glu | GGA Gly | 1655 |
| 483 | GTC Val | AGT Ser | TTC Phe | CCC Pro | TGG Trp | TCC Ser | AGG Arg | CCT Pro | CCC Pro | GGG Gly | CAG Gln | GGG Gly | GAG Glu | 1694 |
| 496 | TTC Phe | AGG Arg | GCC Ala | CTT Leu | AAT Asn | GCT Ala | CGC Arg | CTG Leu | CCC Pro | CTG Leu | AAC Asn | ACT Thr | GAT Asp | 1733 |

FIG. 1B-5

```
509  GCC TAC TTG TCC CTC CAA GAA CTC CAG GGT CAG GAC CCA                                  1772
     Ala Tyr Leu Ser Leu Gln Glu Leu Gln Gly Gln Asp Pro

522  ATC CAC TTG GTG TAG   ACAGATGGCCAGGGTGGGAGGCAGGCAGCT                                  1817
     Thr His Leu Val ***

GCCTGCTCTGCGCCGAGCCCTCAGAAGGACCCTGTTGAGGGTCCCTCAGTCCA
     CTGCTGAGGACACTCAGTGTCCAGTTGCAGCTGGACTTCTCCACCCGGATG
     GCCCCCACCCAGTCCTGCACACTTGGTCCATCCATTTCCAAACCTCCACTG
     CTGCTCCCGGGTCCCTGTGCCCGAGCCAGGAACTGTGTGTTGCAGGGGG
     GCAGTAACTCCCCAACTCCCTCGTTAATCACAGGATCCCACGAATTTAGGC
     TCAGAAGCATCGCTCCTCTCCAGCCCTGCAGCTATTCACCAATATCAGTCC
     TCGCGGCTCTCCAGGGCTCCCTGCCCTCTTCCCACAGGGCAGCCTGAGCGTGC
     CCAGCCTCCTCCTTCCCCCTCCCCGTCCCACGGTTCAAAACCTTGCAC
     TTTCCAAAACCCAAATATGGCCCCCTCAGCCCTTCTGCAATCCTCCCGG
     AGGTCCCACTGCCCTGCCCCTTCTCCAGCCTGGTACTTGTACCTCCGG
     TGTCGTGTGGGGACATCCCCACACCCCTCTGTTGCACATGCTATTCCCTGGGGC
     CACTCAGAGCTCCCTCCCCCCCTCACACCCCTCTAGGTGACAAACTTCCCTGACTCTTCAAGT
     TGCTGTGCGCTCCCCCCCCTCATCTAGGTGACTCTTGACTCTTCAAGT
```

FIG.1B-6

```
GCCGGTTTTGCTTCTCCTGGAGGAAGCACTGCCTCCCTTAATCTGCCAGA
AACTTCTAGCGTCAGTGCTGGAGGGAGAAGCTGTCAGGGACCCAGGGCGCC
TGGAGAAAGAGGCCCTGTTACTATTCCTTTGGGATCTCTGAGGCCTCAGAG
TGCTTGGCTGCTGTATCTCTTTAATGCTGGGGCCCAAGTAAGGCACAGATCC
CCCCGACAAAGTGGATGCCTGCTGCCATCTTCCCACAGTGGCTTCACAGACC
CACAAGAGAAGCTGATGGGGAGTAAACCCTGGAGTCCGAGGCCCAGGCAGC
AGCCCCGCCTAGTGGTGGGCCCTGATGCTGCCAGGCCTGGGACCTCCCACT
GCCCCCTCCACTGGAGGGGTCTCCTCTGCAGCTCAGGGACTGGCACACTGG
CCTCCAGAAGGGCAGCTCCAACACCCGTCGTATACCCCTGGATGAACGAATTAATT
CAGACACAGTGCCACCACCTCGTCTGCCTCCCTGCGCCTGACATTCACACAGAGAG
ACCTGGCACCCAGAGTCCCGTGCCCATTAGGTCTGGCATGCCCCCTCCTGCAAGGGGCTC
GCAGAGTCCCGTGCCCATTAGGTCTGGCATGCCCCCTCCTGCAAGGGGCTC
AACCCCTACCCCGACCCTCCACGTATCTTTCCTAGGCAGATCACGTTGC
AATGCTCAAACAACATTCCACCCCAGCAGGACAGTGACCCCAGTCCCAGC
TAACTCTGACCTGGGAGCCCTCAGGCACCTGCACTTACAGGCCCTTGCTCAC
AGCTGATTGGGCACCTGACCCACACGCCCCACAGGCTCTGACCAGCAGCCT
```

FIG. 1B-7

```
ATGAGGGGTTTGGCACCAAGCTCTGTCCAATCAGGTAGGCTGGGCCTGAA
CTAGCCAATCAGATCAACTCTGTCTTGGGCGTTTGAACTCAGGGAGGAGG
CCCTTGGGAGCCAGGTGCTTGTGGACAAGGCTCCACAAGCGTTGAGCCTTGG
AAAGGTAGACAAGCGTTGAGCCACTAAGCAGAGGACCTTGGGTTCCCAATA
CAAAAATACCTACTGCTGAGAGGGCTGCTGACCATTTGGTCAGGATTCCTG
TTGCCTTTATATCCAAAAATAAAACTCCCCTTTCTTGAGGTTGTCTGAGTCTT
GGGTCTATGCCCTTGAAATGTTTCAGACAGTCTCCACCTCCTGCC
ATAGGGTCCTGAATGTTTCAGACCACTAATCCCTGCTCTTATCCCC
GTTCTGGGCAACCTACTAATCCCTCTGCAAGTCGGTCTCCTTG
CAAATGGAAATTGTATTTTGCCTTTCTCCCACTTTGGGAGGCTCCCACTTCTTG
GGAGGGTTACATTCTTTTAAGTCTTAATCATTTGTGACCATCTTTGTGACATATGTATCTATAC
ATCCGTATCTCTTTTAAGTCAGTTCATTTTCGTTACCATCTTTGTGATTATTTCCTTA
ATATTTTTCTTTAAGTCAGTTCATTTTCGTTGAAATACATTTATAAAGAA
AAATCTTTGTTACTCTGTAAATGAAAAACCCATTTTCGCTATAAATAAAA
GGTAACTGTACAAAATAAGTACAAT
```

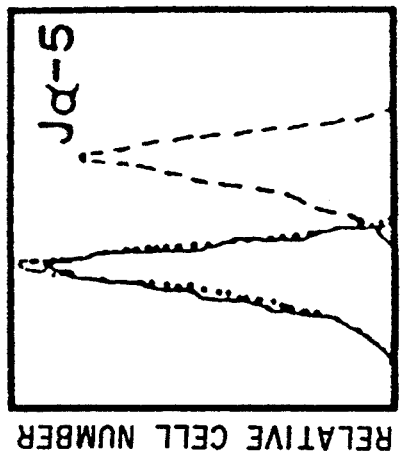
FIG. 4A(3)
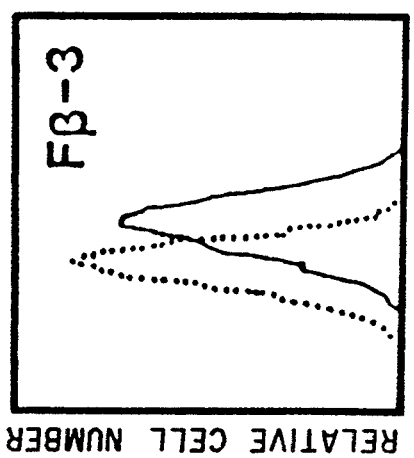
FIG. 4A(6)
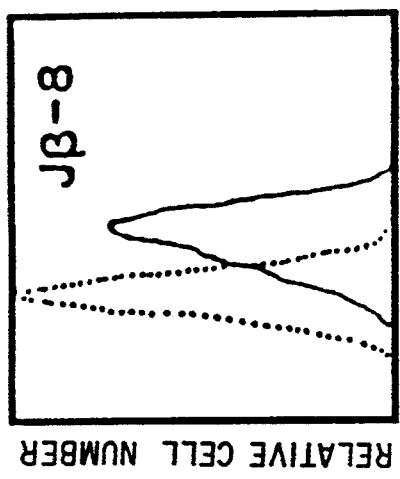
FIG. 4A(2)
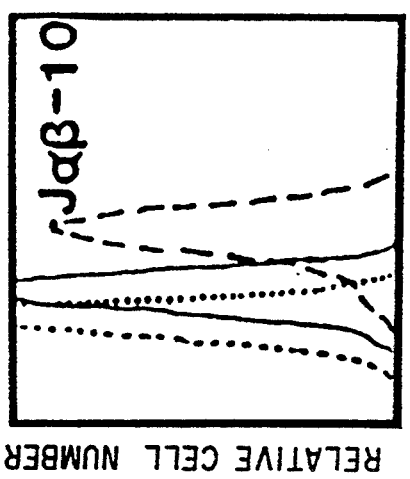
FIG. 4A(5)
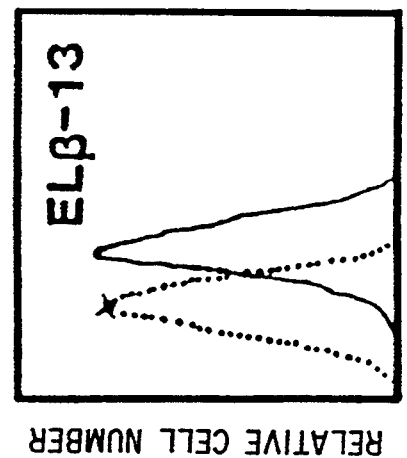
FIG. 4A(1)
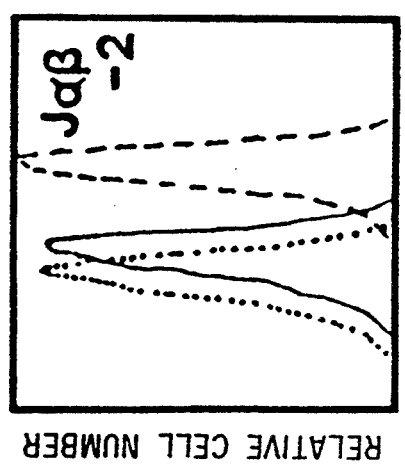
FIG. 4A(4)

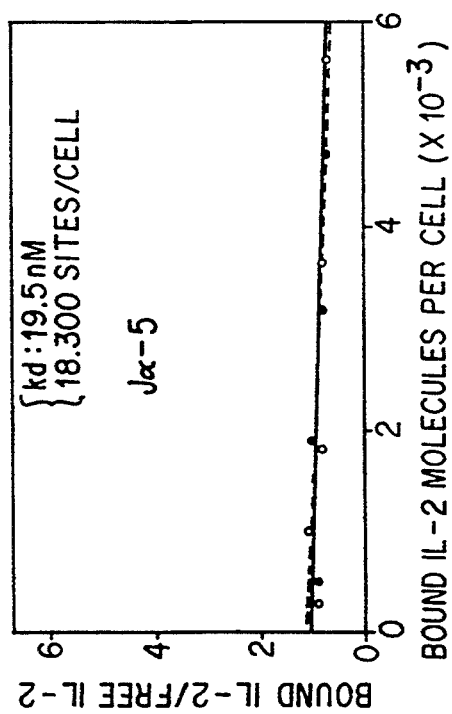
FIG. 4B(3)
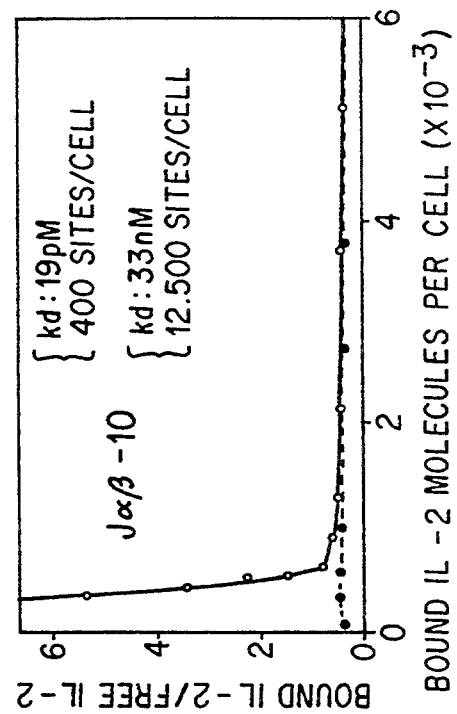
FIG. 4B(5)
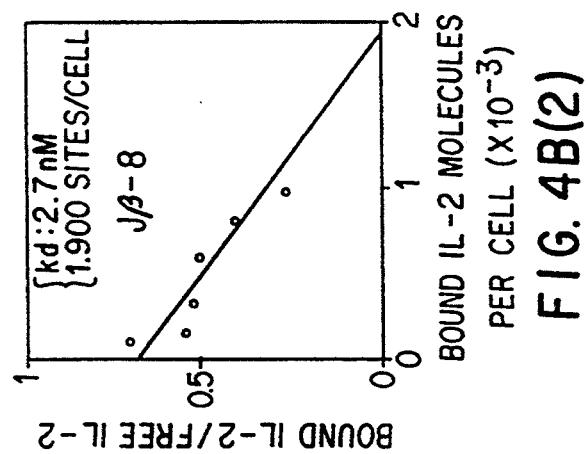
FIG. 4B(2)
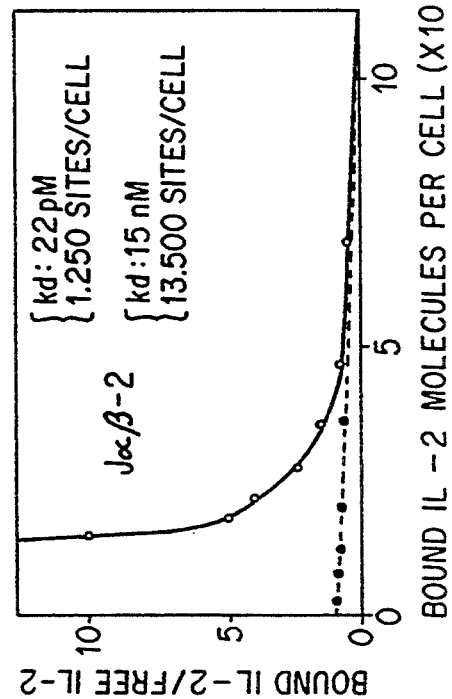
FIG. 4B(4)
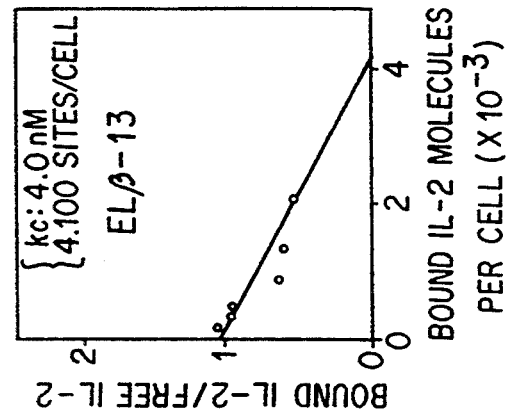
FIG. 4B(1)

```
GAAGATTCTGGTCTGTGGTCTTGGCCGGTGCAAGAACTTTCAGCAGATTCAGAGCTTTCAGAGATCCAGCTGGGGAACCAGAGAGATCCAGTGAGTACGAGGGTTTGCATCCTCTCAGCTGTG  82
GTTACATCACCGGTGCAAGAACTTTCAGAGATTCAGAGCTTCTCTTGCTCTTGAGAACCAGAGAACCAGAGAGATCCAGTGAGTACGAGGGTTTGCATCCTCTCAGCTGTG ATG  377
AACTGTATGAATTCAGAGATTCAGAGCTTTCAGCTGGGGAACCAGAGAGATCCAGTGAGTACGAGGGTTTGCATCCTCTCAGCTGTG ATG  377
                                                                                       Met

GCT ACC ATA GCT CTT CCC TGG AGC CTG TCC CTC CTG TAC GTC TTC CTC ACA CCT TGG GCA TCT GCA  452
Ala Thr Ile Ala Leu Pro Trp Ser Leu Ser Leu Leu Tyr Val Phe Leu Thr Pro Trp Ala Ser Ala

GCA GTG AAA AAC TGT TCC CAT CTT GAA CTT TAC TCA AGA GCC AAT GTC TCT TGC ATG AGC CAT GAA  527
Ala Val Lys Asn Cys Ser His Leu Glu Leu Tyr Ser Arg Ala Asn Val Ser Cys Met Ser His Glu

GAG GCT CTG AAT GTC ACA GTC TTC TGC CAC GTC CAT GCC AAG TGG CGA CAC CTG AAC ACC TGT GAG CTA  602
Glu Ala Leu Asn Val Thr Val Phe Cys His Val His Ala Lys Trp Arg His Leu Asn Thr Cys Glu Leu

ACT CTT GTG AGG CAG GCA GCA ATA TCC AAC TGG GCC CTC TCC CCA GAG TCC TCA CTG ACC TCC  677
Thr Leu Val Arg Gln Ala Ala Ile Ser Asn Trp Ala Leu Ser Pro Glu Ser Phe Leu Thr Ser

GTG GAC CTC CTT GAC CTT AAT AAT GTG GTG GGT AAG GGT CGT AGG GTA AAG ACC TGC TTC CAT  752
Val Asp Leu Leu Asp Ile Asn Val Val Gly Lys Gly Arg Arg Val Lys Thr Cys Phe His

CCC TTT GAC AAC CTC CGC CAG GTC GCC GTG GCC CCT CAT TCC CTC CAA GTT CTG CAC AGA TGT AAC ATA  827
Pro Phe Asp Asn Leu Arg Gln Val Ala Val Ala Pro His Ser Leu Gln Val Leu His Arg Cys Asn Ile

AGC TGG AAG AGG GAT GCA TCC GTA TTA AGC CTC ATT GAT GAA TTT GAG GCC CGT AGA CTT TTG GGC  902
Ser Trp Lys Arg Asp Ala Ser Val Leu Ser Leu Ile Asp Glu Phe Glu Ala Arg Arg Leu Leu Gly

CAC AGC TGG GAG GAT GTC AAA GTC AGG CAG ATC CAC TAC ATT GAA CCA ACG TGG CTC TTC ATC CCT  977
His Ser Trp Glu Asp Val Lys Val Arg Gln Ile His Tyr Ile Glu Pro Thr Trp Leu Phe Ile Pro

AGT ACC TCA TAT GAG TGG GAT GTC CAG AGG CCA GCA GAT CCC AAG CAG CGA AAT GCT CAA GGG ACC TGG AGT CCC AGA CAG  1052
Ser Thr Ser Tyr Glu Trp Asp Val Gln Arg Pro Ala Asp Pro Lys Gln Arg Asn Ala Gln Gly Thr Trp Ser Pro Arg Gln

CCC CTG ACC CTT TGG GGT TGT TCT TTT AGG AGG ACA AGG CCA GCA GAT CCC ATG AAG GAG ATC CTC CCC ATG TCA AGA CTT CTG  1127
Pro Leu Thr Leu Trp Gly Cys Ser Phe Arg Arg Thr Arg Pro Ala Asp Pro Met Lys Glu Ile Leu Pro Met Ser Arg Leu Leu

CTG GTC CTT GGT TGT TTT TCT GGC TTC TTC TCC TGC TAC ATT TTG TAC ATT TTG AAG GTC TTG XXX CGG TAC CTT GGG CCA TGG  1202
Leu Val Leu Gly Cys Cas Phe Ser Gly Phe Phe Ser Cys Tyr Ile Leu Tyr Ile Leu Val Lys Y   Arg Tyr Leu Gly Pro Trp
```

RECOMBINANT PROTEIN RECEPTOR FOR IL-2

This application is a continuation of application Ser. No. 07/865,155, filed Apr. 8, 1992, now abandoned, which is a division of application Ser. No. 07/487,059, filed Mar. 5, 1990, now U.S. Pat. No. 5,198,359.

FIELD OF THE INVENTION

This invention is in the field of recombinant genetics. In particular, this invention relates to receptors for interleukin-2, more particularly to the β-chain of the receptor, and to cDNA coding for the β-chain or fragments thereof, vectors containing cDNA inserts coding for the β-chain, hosts transformed by such vectors and the cultivation of such hosts to produce said β-chain.

BACKGROUND OF THE INVENTION

Ample evidence has been accumulated that cytokines, a class of soluble mediators involved in cell-to-cell "communications," are essential in the regulation of the immune system. It has been known that cytokines induce proliferation, differentiation and activation of target cells through interaction with specific cell surface receptor(s). Interleukin-2 (IL-2), previously defined as T cell growth factor (Morgan, D. A., et al., *Science* 198:1007 (1976)), is one of the best characterized cytokines and is known to play a pivotal role in the antigen-specific clonal proliferation of T lymphocytes (T cells) (Smith, K. A., *Ann. Rev. Immunol.* 2:319 (1984); Taniguchi, T., et al., *Immunol. Rev.* 92:121 (1986)). IL-2 also appears to act on other cells of the immune system such as immature thymocytes (Raulet, D. H., *Nature* 314:101 (1985)), B lymphocytes (B cells) (Tsudo, M., et al., *J. Exp. Med.* 160:612 (1984); Waldmann, T. A., et al., *J. Exp. Med.* 160:1450 (1984); Blackman, M. A., et al., *Cell* 47:609 (1986)), macrophages (Malkovsky, M., et al., *Nature* 325:262 (1987)), natural killer cells (NK cells) (Henney, C. S., et al., *Nature* 291:335 (1981)), and lymphokine-activated killer cells (LAK cells) (Lotze, M. E., et al., *Cancer Res.* 41:4420 (1981); Grimm, E. A., et al., *J. Exp. Med.* 155:1823 (1982)). These multifunctional properties of IL-2 have now opened up possibilities in the formulation of immunotherapies such as adoptive immunotherapy (Rosenberg, S. A., et al., *N. Engl. J. Med.* 316:889 (1987)). More recently, IL-2 has been shown to function also on neural cells such as oligodendrocytes (Benveniste, E. N., et al., *Nature* 321:610 (1986)), suggesting a possible involvement of this cytokine in the central nervous system. Despite extensive studies on the IL-2 system in the context of basic and clinical immunology, information has been limited on the molecular mechanism(s) underlying the IL-2-mediated signal transduction (LeGrue, S. J., *Lymphokine Res.* 7:1987 (1988); Millis, G. B., et al., *Cell* 55:91 (1988); Valge, V. E., et al., *Cell* 55:101 (1988); Tigges, M. A., et al., *Science* 243:781 (1989)).

The IL-2 receptor (IL 2R) is known to be uniquely present in three forms: high-, intermediate- and low-affinity forms with respect to its binding ability to IL-2, and respective dissociation constants (Kds) of $10^{-11}$M, $10^{-9}$M, and $10^{-8}$M (Robb, R. J., et al., *J. Exp. Med.* 160:1126 (1984); Tsudo, M., et al., *Proc. Natl. Acad. Sci. USA* 83:9694 (1986); Teshigawara, K., et al., *J. Exp. Med.* 165:223 (1987)). Following the characterization of IL-2Rα chain (Tac antigen, p55) (Leonard, W. J., et al., *Nature* 311:626 (1984); Nikaido, T., et al., *Nature* 311:631 (1984); Cosman, D., et al., *Nature* 312:768 (1984)), it became evident that the α chain constitutes solely the low-affinity form and it is not functional per se in IL-2 internalization and signal transduction, unless associated with another specific membrane component(s) of lymphoid cells (Hatakeyama, M., et al., *Nature* 318:467 (1985); Greene, W. C., et al., *J. Exp. Med.* 162:363 (1985); Kondo, S., et al., *J. Exp. Med.* 320:75 (1986); Robb, R. J., *Proc. Natl. Acad. Sci. USA* 83:3992 (1986)). Subsequently, the lymphoid membrane component was identified to be a novel receptor chain, termed β-chain (or p70–75) (Tsudo, M., et al., *Proc. Natl. Acad. Sci. USA* 83:9694 (1986); Teshigawara, K., et al., *J. Exp. Med.* 165:223 (1987); Sharon, M., et al., *Science* 234:859 (1986); Robb, R. J., et al., *Proc. Natl. Acad. Sci. USA* 84:2002 (1987); Tsudo, M., et al., *Proc. Natl. Acad. Sci. USA* 84:4215 (1987); Dukovich, M., et al., *Nature* 327:518 (1987)). In fact, experimental evidence has suggested that the IL-2Rβ chain per se constitutes the intermediate-affinity form (Tsudo, M., et al., *Proc. Natl. Acad. Sci. USA* 83:9694 (1986); Teshigawara, K., et al., *J. Exp. Med.* 165:223 (1987)). In addition, its association with the IL-2Rα chain results in the high-affinity form of the receptor (Tsudo, M., et al., *Proc. Natl. Acad. Sci. USA* 83:9694 (1986); Teshigawara, K., et al., *J. Exp. Med.* 165:223 (1987); Sharon, M., et al., *Science* 234:859 (1986); Robb, R. J., et al., *Proc. Natl. Acad. Sci. USA* 84:2002 (1987); Tsudo, M., et al., *Proc. Natl. Acad. Sci. USA* 84:4215 (1987); Dukovich, M., et al., *Nature* 327:518 (1987)). Expression studies using wild-type and mutated IL-2Rα chain cDNAs strongly support the notion that the IL-2Rβ chain but not the IL-2Rα chain possesses a domain(s) responsible for driving the intracellular signal transduction pathway(s) (Hatakeyama, M., et al., *J. Exp. Med.* 166:362 (1987); Kondo, S., et al., *Nature* 327:64 (1987)). There exists, therefore, a need to obtain IL-2β chain in amounts which will enable its structure and function to be elucidated, this being an essential step in gaining further insight into the molecular basis of the high-affinity of IL-2R as well as on the mechanism of signal transduction operating in IL-2 responsive cells.

SUMMARY OF THE INVENTION

In order to satisfy the need mentioned above, cDNA coding for the IL-2Rβ chain or fragments thereof have been prepared whereby insertion of said cDNA in a suitable vector and expression thereof in an appropriate host enables recombinant and large-scale production of protein corresponding to the IL-2Rβ chain or fragments thereof having affinity to the IL-2R.

According to one aspect of the present invention, therefore, recombinant cDNA coding for an IL-2Rβ chain or a fragment thereof is provided.

The cDNA of the invention may have the formula:

```
                                                          ATG
GCG GCC CCT GCT CTG TCC TGG CGT CTG CCC CTC CTC ATC
CTC CTC CTG CCC CTG GCT ACC TCT TGG GCA TCT GCA GCG
```

-continued

```
GTG AAT GGC ACT TCC CAG TTC AGA TGC TTC TAC AAC TCG
AGA GCC AAC ATC TCC TGT CTC TGG AGC CAA GAT GGG GCT
CTG CAG GAC ACT TCC TGC AAG TCA TGC CTG GCC GAC
AGA CGG CGG TGG AAC CAA ACC TGT GAG CTG CTC CCC GTG
AGT CAA GCA TCC TGG GCC TGC AAC CTG ATC CTC GGA GCC
CCA GAT TCT CAG AAA CTG ACC ACA GTT GAC ATC GTC ACC
CTG AGG GTG CTG TGC CGT GAG GGG GTG CGA TGG AGG GTG
ATG GCC ATC CAG GAC TTC AAG CCC TTT GAG AAC CTT CGC
CTG ATG GCC CCC ATC TCC CTC CAA GTT GTC CAC GTG GAG
ACC CAC AGA TGG AAC ATA AGC TGG GAA ATC TCC CAA GCC
TCC CAC TAC TTT GAA AGA CAC CTG GAG TTC GAG GCC CGG
ACG CTG TCC CCA GGC CAC ACC TGG GAG GAG GCC CCC CTG
CTG ACT CTC AAG CAG AAG CAG GAA TGG ATC TGC CTG GAG
ACG CTC ACC CCA GAC ACC CAG TAT GAG TTT CAG GTG CGG
GTC AAG CCT CTG CAA GGC GAG TTC ACG ACC TGG AGC CCC
TGG AGC CAG CCC CTG GCC TTC AGG ACA AAG CCT GCA GCC
CTT GGG AAG GAC ACC ATT CCG TGG CTC GGC CAC CTC CTC
GTG GGC CTC AGC GGG GCT TTT GGC TTC ATC ATC TTA GTG
TAC TTG CTG ATC AAC TGC AGG AAC ACC GGG CCA TGG CTG
AAG AAG CTC CTG AAG TGT AAC ACC CCA GAC CCC TCG AAG
TTC TTT TCC CAG CTG AGC TCA GAG CAT GGA GGA GAC GTC
CAG AAG TGG CTC TCT TCG CCC TTC CCC TGA TCG TCC TTC
AGC CCT GGC GGC CTG GCA CCT GAG ATC TCG CCA CTA GAA
GTG CTG GAG AGG GAC AAG GTG ACG CAG CTG CTC CTG CAG
CAG GAC AAG GTG CCT GAG CCC GCA TCC TTA AGC AGC AAC
CAC TCG CTG ACC AGC TGC TTC ACC AAC CAG GGT TAC TTC
TTC TTC CAC CTC CCG GAT GCC TTG GAG ATA GAG GCC TGC
CAG GTG TAC TTT ACT TAC GAC CCC TAC TCA GAG GAA GAC
CCT GAT GAG GGT GTG GCC GGG GCA CCC ACA GGG TCT TCC
CCC CAA CCC TTG CAG CCT CTG TCA GGG GAG GAC GAC GCC
TAC TGC ACC TTC CCC TCC AGG GAT GAC CTG CTG CTC TTC
TCC CCC AGT CTC CTC GGT GGC CCC AGC CCC CCA AGC ACT
GCC CCT GGG GGC AGT GGG GCC GGT GAA GAG AGG ATG CCC
CCT TCT TTG CAA GAA AGA GTC CCC AGA GAC TGG GAC CCC
CAG CCC CTG GGG CCT CCC ACC CCA GGA GTC CCA GAC CTG
GTG GAT TTT CAG CCA CCC CCT GAG CTG GTG CTG CGA GAG
GCT GGG GAG GAG GTC CCT GAC GCT GGC CCC AGG GAG GGA
GTC AGT TTC CCC TGG TCC AGG CCT CCT GGG CAG GGG GAG
TTC AGG GCC CTT AAT GCT CGC CTG CCC CTG AAC ACT GAT
GCC TAC TTG TCC CTC CAA GAA CTC CAG GGT CAG GAC CCA
ATC CAC TTG GTG TAG
``` which codes for human IL-2Rβ, or a degenerate variant thereof. The invention also relates to fragments of the cDNA coding for fragments of human IL-2Rβ which bind to the IL-2 receptor.

Another cDNA of the invention, for example, has the formula:

```
                                                                                                                                                                                                                                ATG
GCT ACC ATA GCT CTT CCC TGG AGC CTG TCC CTC TAC GTC TTC CTC CTG CTG GCT ACA CCT TGG GCA TCT GCA
GCA GTG AAA AAC TGT TCC CAT CTT GAA TGC CAT TCA AGA GCC AAT GTC TCT TGC ATG TGG AGC CAT GAA
GAG GCT CTG AAT GTC CTG CAC TGC CAC AAG CTG CGA CAC CTG AAC ACC TGT GAG CTA
ACT CTT GTG AGG CAG GCA TCC TGG GCC TGC AAC CTG ATC CTC GGG TCG TTC CCA GAG TCA CTG ACC TCC
GTG GAC CTC TTT GAC AAC CTC CGT AGG AAG GTA AAG ACC TGC GAC TTC CAT
CCC TTT GAC AAC CTT CGC CTG GTG GCC CCT CAT TCC ATT GAT ACC AGA TGT AAC ATA
AGC TGG AAG GTC TCC CAG GTC TCT CAC TAC TTG GAA TTT GAG GCC CGT AGA CGT CTT CTG GGC
CAC AGC TGG GAG GAT GCA TCC GTA TTA AGC CTC AAG CAG ACG TGG CTC TTG GAG ATG CTG ATC CCT
AGT ACC TCA TAT GAG GTC CAG GTG AGG CCA GTC AAA GCT CAA CGA AAC CGA AAC CTG GGC ACC TGG AGC CAG
CCC CTG ACC TTT CGG ACA AGG CCA GCA GAT CCC TTC TCC ATG AAG GAG ATC CTC CCC ATG TCA XXX CGG TAC CTT GGG CCA TGG
CTG GTC CTT GGT TGT TCT AAG TGC CAC ATC CCA GAT CCT GAG TTC TCC TTT TGC CAG CTG AGC TCC CAG CAT GGG GGA
GAC CTT CAG ACA GTT CTC TCC TCG CCT CTG TCC TTC AGC CCC CTA CAG AAG GCC CCT GCC CCT GAG ATC TCT
CCG CTG GAA GTG CTC GAC GGA GAT CCC AAG GCC GTG CAG CTG TTA CAG AAG TCT GCA AAT GCC CTG TAC CCC
TCG CCC AGC GGC CAC TCA CAG GTG TAC TTC ACC AAC CAG GTG GAA GAC CCT GTG TGC CCC AAT GCC TTG
GAG ATC GAA TCC TGC CAG GGA TCT GCC CCA CCT CTG GCT CCT CTG GAA GAA CAG GAT GAC TAT GCC TTC CCG CCC
CTG CCC GAG TCT GAT GTG CTG CTG CTC TCC CCG CTC GAT GAG GGA CTT CCA ATG AGC TGC AGA GCC CCT GAA
GAA AGA TCT CCA CTC CCT CAT GAG GGA CTT GCC AAT AGC TCT GAC CGC ATG GGC GAG CAG CTG TTA CAG CGC CCT
CTG GAG CGG ATG CCG GAA GGT GAT GAG GGG CTG TCT CTG GGA GAG CAG AGT GTC CCA GAA
GGC AAC CTT CAT GGG CAA GAT CAG GCC CAG GGC CCC ATC ACC CTG ACC GAT TCA GTC CAC CTA ATA TAG
CTT CAA GAA CTA CAG GCC CAA GAT TCA GTC CAC CTA ATA TAG

XXX = GGC or TGC
``` which codes for murine IL-2Rβ, or a degenerate variant thereof. The invention also relates to fragments of the cDNA coding for fragments of murine IL-2Rβ which bind to the IL-2 receptor.

DESCRIPTION OF THE FIGURES

FIGS. 1A and 1B (1–8) show the structure of the human IL-2Rβ chain cDNA.

FIG. 4A (1–6) illustrates the expression of human IL-2Rα and/or IL-2Rβ chain cDNAs by means of cell surface staining patterns of human IL-2Rα and/or IL-2Rβ cDNA transfectants. FIG. 4B (1–5) illustrates the expression of the α and β chains by means of the Scatchard plot analysis of $^{125}$I-IL-2 binding to the transfectants expressing the cloned cDNAs.

FIGS. 8A and 8B depicts the DNA and amino acid sequence of the structural gene for murine IL-2Rβ in clone pMIL-2Rβ36.

DESCRIPTION OF THE PREFERRED EMBODIMENTS

Figure 1A:
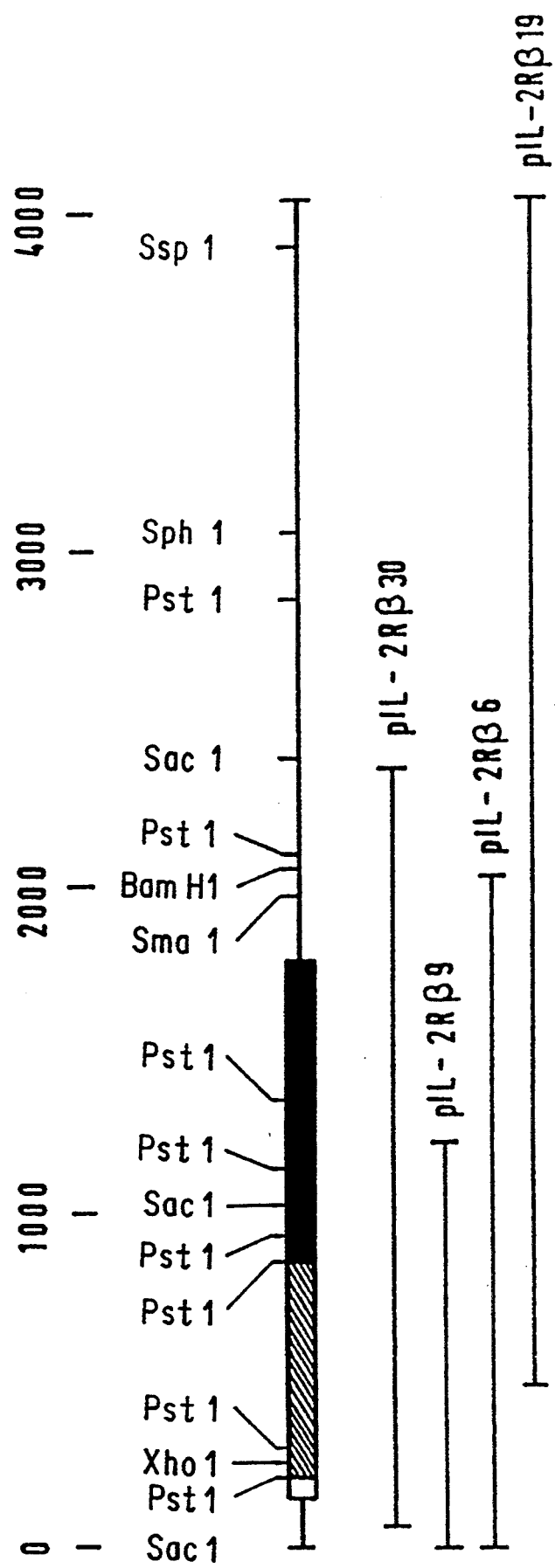

The present invention relates to receptors for interleukin-2 (IL-2), more particularly to the β-chain of the receptor, and to cDNA coding for the β-chain or fragments thereof, vectors containing cDNA inserts coding for the β-chain, hosts transformed by such vectors and the cultivation of such hosts to produce said β-chain. In particular, the present invention is directed to DNA coding for fragments of the IL-2Rβ, for instance the extracellular part or a fragment thereof or the intracellular part or a fragment thereof.

Of special interest are those DNAs coding for fragments of IL2-Rβ which are soluble, these including the extracellular parts and fragments thereof.

Figure 8B:
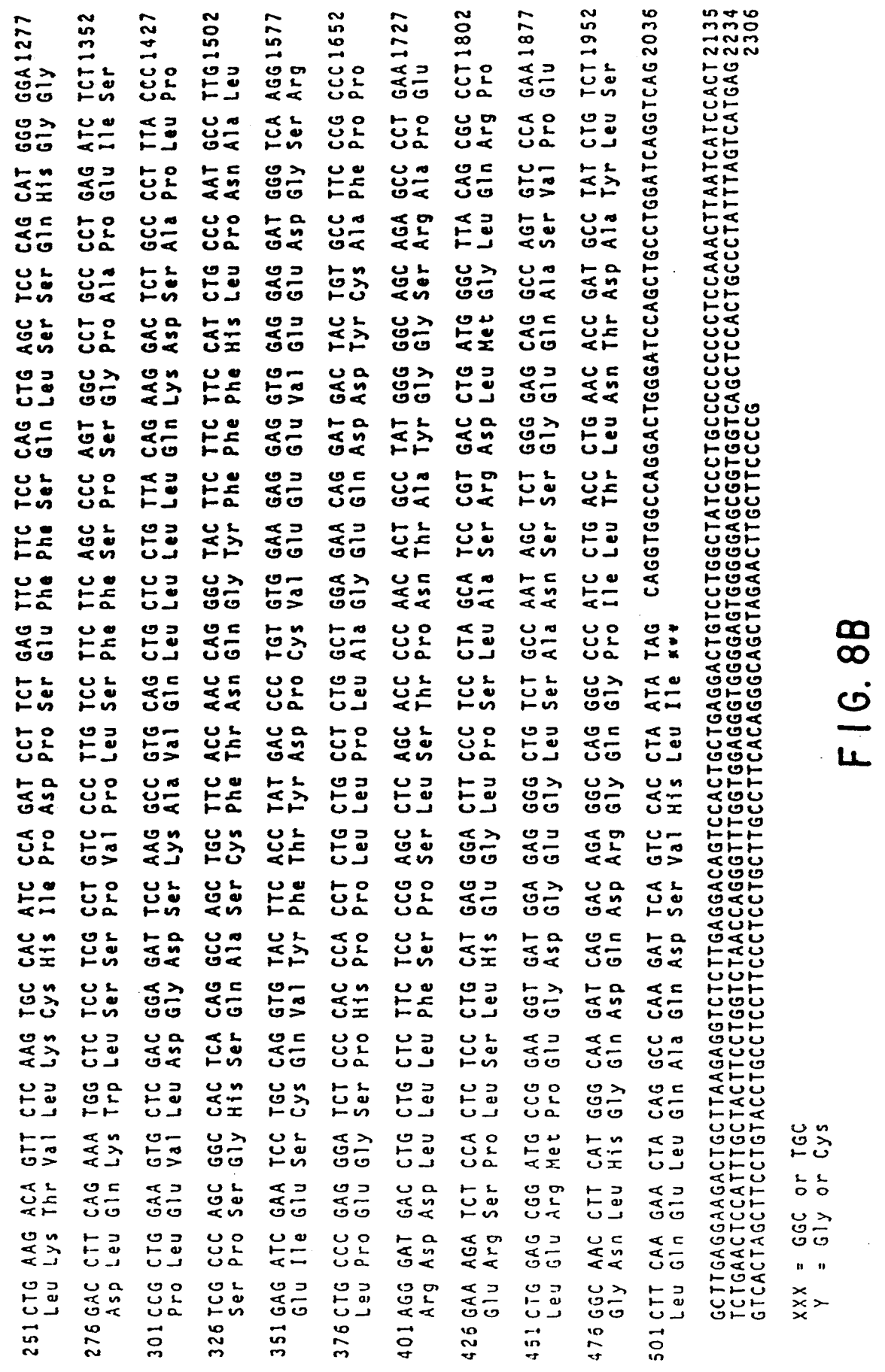

The present invention thus also includes within its scope cDNA coding for fragments of the above-mentioned cDNAs, e.g., portions of the complete sequence of the hIL-2Rβ chain, for example, the extracellular portion beginning at, or about amino acid (a.a.) (see FIG. 1B) 1 e.g., 1, 2, 3, 4, 5, 6, 7, 8, 9, 10 and ending at or about a.a. 214, e.g., 200, 201, 202, 203, 204, 205, 206, 207, 208, 209, 210, 211, 212, 213, 214, 215, 216, 217, 218, 219, 220, or sub-fragments of this extracellular part or degenerate variants thereof, or fragments corresponding to the intracellular part of the receptor chain, e.g., the portion beginning at or about a.a. 239, e.g., a.a. 230, 231, 232, 234, 235, 236, 237, 238, 239, 240, 241, 242, up to or about the end a.a. 525, e.g., 516, 517, 518, 519, 520, 521, 522, 523, 524 and 525 or sub-fragments thereof, or degenerate variants thereof, as well as cDNA coding for fragments of the complete sequence of the murine IL-2Rβ chain (see FIGS. 8A and 8B), for example, the extracellular part beginning at, or about, a.a. 1, e.g., 1, 2, 3, 4, 5, 6, 7, 8, 9, 10 and ending at or about a.a. 210, e.g., 200, 201, 202, 203, 204, 205, 206, 207, 208, 209, 210, 211, 212, 213, 214, 215, 216, 217, 218, 219, 220, or sub-fragments of this extracellular part or degenerate variants thereof, or fragments corresponding to the intracellular part of the receptor chain, e.g., the portion beginning at or about a.a. 235, e.g., a.a. 225, 226, 227, 228, 229, 230, 231, 232, 233, 234, 235, 236, 237, 238, 239, 240, 241, 242, up to or about the end a.a. 513, e.g., 505, 506, 507, 508, 509, 510, 512, and 513 or sub-fragments thereof, or degenerate variants thereof.

It will be understood that for the particular IL-2Rβ chains or portions thereof described herein, natural allelic variations may exist, occurring from individual to individual. These variations may be demonstrated by one or more amino acid differences in the overall sequence or by deletions, substitutions, insertions, inversions or additions of one or more amino acids in the sequence. In addition, it will be understood that the IL-2Rβ chain or portions thereof described herein may be modified by genetic engineering techniques, e.g., point mutation, for the substitution, deletion or addition of one or more amino acids without changing the essential characteristics of the IL-2Rβ chain or portion thereof.

The present invention thus also includes within its scope DNA sequences capable of hybridizing, preferably under stringent conditions, with the DNA sequences described herein and coding for proteins having substantially the activity of an IL-2Rβ chain or portions thereof, especially soluble IL-2Rβ fragments. Stringent hybridization conditions select for DNA sequences of greater than 85% or, more preferably, greater than about 90% homology. Screening of the cDNA library may be carried out under highly stringent conditions according to the method described in European Patent Application No. 88 119 602.9 and Kashima et al. (*Nature* 313:402–404 (1985)). The DNA sequences capable of hybridizing under stringent conditions with the DNA sequences disclosed in the present application may be, for example, allelic variants of the disclosed DNA sequences, may be naturally present in the human or mouse but related to the disclosed DNA sequences, or may derived from other animal sources. General techniques of nucleic acid hybridization are disclosed by Maniatis, T. et al., In: *Molecular Cloning, a Laboratory Manual*, Coldspring Harbor, N.Y. (1982), and by Haymes, B. D. et al., In: *Nucleic Acid Hybridization, a Practical Approach*, IRL Press, Washington, D.C. (1985), which references are herein incorporated by reference.

In one further aspect of the invention is provided a recombinant DNA molecule coding for a soluble fragment of the human IL2-Rβ (hIL2-Rβ), for example, an amino acid sequence comprising the amino acids about 1 to about 210 of the entire hIL2-Rβ. Such a DNA molecule may code, for example, for a soluble human interleukin 2 receptor β-chain derivative having 212 amino acid residues in which residues 1 to 210 correspond to the amino acids of the native IL-2R β-chain.

For example, in one embodiment described below, the terminal nucleotides of a cDNA molecule coding for a soluble hIL-2Rβ derivative are as follows:

```
    GCC CTT GCT AGC TAG
208 Ala Leu Ala Ser [Stop]
```

Using standard techniques of recombinant DNA technology, vectors for transforming suitable host cells can be constructed which contain cDNA sequences corresponding to the structural gene for IL-2Rβ as set forth above or any desired fragment thereof, or degenerate variant thereof.

Suitable vectors, for example, are plasmid vectors for example and include control and regulatory sequences operably linked to the cDNA sequence coding for the IL-2Rβ chain or fragment thereof.

Suitable techniques are well known and widely practiced and by, way of example are described, in connection with other proteins, in European Patent Application, Publication Nos. 0254249 and 0170204 whose disclosures are fully incorporated by reference herein.

Any of a variety of procedures may be used to clone the IL-2Rβ chain or fragment thereof. A preferred method is the taught by Seed et al., *Proc. Natl. Acad. Sci. USA* 84:3365 (1987); and Seed, B. et al., *Nature* 328:840 (1987), the disclosures of which are hereby incorporated by reference in their entirety.

Another such method entails analyzing a shuttle vector library of cDNA inserts (derived from an IL-2Rβ expressing cell) for the presence of an insert which contains the IL-2Rβ gene. Such an analysis may be conducted by transfecting cells with the vector and then assaying for IL-2Rβ expression. A preferred method for cloning this gene entails determining the amino acid sequence of the IL-2Rβ molecule. To accomplish this task IL-2Rβ protein may be purified and analyzed by automated sequentors. Alternatively, the molecule may be fragmented as with cyanogen bromide, or with proteases such as papain, chymotrypsin or trypsin (Oike, Y. et al., *J. Biol. Chem.* 257:9751–9758 (1982); Liu, C. et al., *Int. J. Pept. Protein Res.* 21:209–215 (1983)). Although it is possible to determine the entire amino acid sequence of IL-2Rβ, it is preferable to determine the sequence of peptide fragments of the molecule. If the peptides are greater than 10 amino acids long, the sequence information is generally sufficient to permit one to clone a gene such as the gene for IL-2Rβ.

The sequence of amino acid residues in a peptide is designated herein either through the use of their commonly employed 3-letter designations or by their single-letter designations. A listing of these 3-letter and 1-letter designations may be found in textbooks such as *Biochemistry*, Lehninger, A., Worth Publishers, New York, N.Y. (1970). When such a sequence is listed vertically, the amino terminal residue is intended to be at the top of the list, and the carboxy terminal residue of the peptide is intended to be at the bottom of the list. Similarly, when listed horizontally, the amino terminus is intended to be on the left end whereas the carboxy terminus is intended to be at the right end. The residues of amino acids in a peptide may be separated by hyphens. Such hyphens are intended solely to facilitate the presentation of a sequence. As a purely illustrative example, the amino acid sequence designated:

-Gly-Ala-Ser-Pheindicates that an Ala residue is linked to the carboxy group of Gly, and that a Ser residue is linked to the carboxy group of the Ala residue and to the amino group of a Phe residue. The designation further indicates that the amino acid sequence contains the tetrapeptide Gly-Ala-Ser-Phe. The designation is not intended to limit the amino acid sequence to this one tetrapeptide, but is intended to include (1) the tetrapeptide having one or more amino acid residues linked to either its amino or carboxy end, (2) the tetrapeptide having one or more amino acid residues linked to both its amino and its carboxy ends, (3) the tetrapeptide having no additional amino acid residues.

Once one or more suitable peptide fragments have been sequenced, the DNA sequences capable of encoding them are examined. Because the genetic code is degenerate, more than one codon may be used to encode a particular amino acid (Watson, J. D., In: *Molecular Biology of the Gene*, 3rd Ed., W. A. Benjamin, Inc., Menlo Park, Calif. (1977), pp. 356–357). The peptide fragments are analyzed to identify sequences of amino acids which may be encoded by oligonucleotides having the lowest degree of degeneracy. This is preferably accomplished by identifying sequences that contain amino acids which are encoded by only a single codon. Although occasionally such amino acid sequences may be encoded by only a single oligonucleotide, frequently the amino acid sequence can be encoded by any of a set of similar oligonucleotides. Importantly, whereas all of the members of the set contain oligonucleotides which are capable of encoding the peptide fragment and, thus, potentially contain the same nucleotide sequence as the gene which encodes the peptide fragment, only one member of the set contains a nucleotide sequence that is identical to the nucleotide sequence of this gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

In a manner exactly analogous to that described above, one may employ an oligonucleotide (or set of oligonucleotides) which have a nucleotide sequence that is complementary to the oligonucleotide sequence or set of sequences that is capable of encoding the peptide fragment.

A suitable oligonucleotide, or set of oligonucleotides which is capable of encoding a fragment of the IL-2Rβ gene (or which is complementary to such an oligonucleotide, or set of oligonucleotides) is identified (using the above-described procedure), synthesized, and hybridized, by means well known in the art, against a DNA or, more preferably, a cDNA preparation derived from human cells which are capable of expressing IL-2Rβ gene sequences. Techniques of nucleic acid hybridization are disclosed by Maniatis, T. et al., In: *Molecular Cloning, a Laboratory Manual*, Coldspring Harbor, N.Y. (1982), and by Haymes, B. D. et al., In: *Nucleic Acid Hybridization, a Practical Approach*, IRL Press, Washington, D.C. (1985), which references are herein incorporated by reference. The source of DNA or cDNA used will preferably have been enriched for IL-2Rβ sequences. Such enrichment can most easily be obtained from cDNA obtained by extracting RNA from cells cultured under conditions which induce IL-2Rβ synthesis.

Techniques such as, or similar to, those described above have successfully enabled the cloning of genes for human aldehyde dehydrogenases (Hsu, L. C. et al., *Proc. Natl. Acad. Sci. USA* 82:3771–3775 (1985)), fibronectin (Suzuki, S. et al., *Eur. Mol. Biol. Organ. J.* 4:2519–2524 (1985)), the human estrogen receptor gene (Walter, P. et al., *Proc. Natl. Acad. Sci. USA* 82:7889–7893 (1985)), tissue-type plasminogen activator (Pennica, D. et al., *Nature* 301:214–221 (1983)) and human term placental alkaline phosphatase complementary DNA (Kam, W. et al., *Proc. Natl. Acad. Sci. USA* 82:8715–8719 (1985)).

In a preferred alternative way of cloning the IL-2Rβ gene, a library of expression vectors is prepared by cloning DNA or, more preferably cDNA, from a cell capable of expressing IL-2Rβ into an expression vector. The library is then screened for members capable of expressing a protein which binds to anti-IL-2Rβ antibody, and which has a nucleotide sequence that is capable of encoding polypeptides that have the same amino acid sequence as IL-2Rβ chain or fragment thereof.

The cloned IL-2Rβ gene, obtained through the methods described above, may be operably linked to an expression vector, and introduced into bacterial, or eukaryotic cells to produce IL-2Rβ protein. Techniques for such manipulations are disclosed by Maniatis, T. et al., supra, and are well known in the art.

In the event that the expressed molecule is unable to bind to IL-2, it may be concluded that the isolated sequence encodes only a fragment of the desired gene sequence. Accordingly, the isolated gene sequence is used to identify and isolate any missing fragments of the desired gene sequence (Bender, W. et al., *J. Supramolec. Struc.* 10(suppl.):32 (1979); Chinault, A. C., et al., *Gene* 5:111 (1979); Clarke, L. et al., *Nature* 287:504 (1980)). Once any such sequences have been identified and isolated, it is possible to construct a single gene sequence which is capable of encoding the entire desired receptor molecule using well known methods of recombinant DNA technology.

DNA or cDNA molecules which encode the receptor molecule can be operably linked into an expression vector and introduced into a host cell to enable the expression of the receptor molecule by that cell. Two DNA sequences (such as a promoter region sequence and a desired receptor molecule encoding sequence) are said to be operably linked if the nature of the linkage between the two DNA sequences does not (1) result in the introduction of a frame-shift mutation, (2) interfere with the ability of the promoter region sequence to direct the transcription of the desired receptor molecule encoding gene sequence, or (3) interfere with the ability of the desired receptor molecule gene sequence to be transcribed by the promoter region sequence.

A DNA sequence encoding the receptor molecule may be recombined with vector DNA in accordance with conventional techniques, including blunt-ended or stagger-ended termini for ligation, restriction receptor molecule digestion to provide appropriate termini, filling in of cohesive ends as appropriate, alkaline phosphatase treatment to avoid undesirable joining, and ligation with appropriate ligases.

The present invention encompasses the expression of the desired receptor molecule in either prokaryotic or eukaryotic cells. Preferred eukaryotic hosts include yeast (especially Saccharomyces), fungi (especially Aspergillus), mammalian cells (such as, for example, human or primate cells) either in vivo, or in tissue culture.

Yeast and mammalian cells are preferred hosts of the present invention. The use of such hosts provides substantial advantages in that they can also carry out post-translational peptide modifications including glycosylation. A number of recombinant DNA strategies exist which utilize strong promoter sequences and high copy number of plasmids which can be utilized for production of the desired proteins in these hosts.

Yeast recognize leader sequences on cloned mammalian gene products and secrete peptides bearing leader sequences (i.e., pre-peptides). Mammalian cells provide post-translational modifications to protein molecules including correct folding or glycosylation at correct sites.

Mammalian cells which may be useful as hosts include cells of fibroblast origin such as VERO or CHO-K1, and their derivatives. For a mammalian host, several possible vector systems are available for the expression of the desired receptor molecule. A wide variety of transcriptional and translational regulatory sequences may be employed, depending upon the nature of the host. The transcriptional and translational regulatory signals may be derived from viral sources, such as adenovirus, bovine papilloma virus, simian virus, or the like, where the regulatory signals are associated with a particular gene which has a high level of expression. Alternatively, promoters from mammalian expression products, such as actin, collagen, myosin, etc., may be employed. Transcriptional initiation regulatory signals may be selected which allow for repression or activation, so that expression of the genes can be modulated. Of interest are regulatory signals which are temperature-sensitive so that by varying the temperature, expression can be repressed or initiated, or are subject to chemical regulation, e.g., metabolite.

The expression of the desired receptor molecule in eukaryotic hosts requires the use of eukaryotic regulatory regions. Such regions will, in general, include a promoter region sufficient to direct the initiation of RNA synthesis. Preferred eukaryotic promoters include the promoter of the mouse metallothionein I gene (Hamer, D., et al., *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature (London)* 290:304–310 (1981)); the yeast gal4 gene promoter (Johnston, S. A., et al., *Proc. Natl. Acad. Sci. (USA)* 79:6971–6975 (1982); Silver, P. A., et al., *Proc. Natl. Acad. Sci. (USA)* 81:5951–5955 (1984)).

As is widely known, translation of eukaryotic mRNA is initiated at the codon which encodes the first methionine. For this reason, it is preferable to ensure that the linkage between a eukaryotic promoter and a DNA sequence which encodes the desired receptor molecule does not contain any intervening codons which are capable of encoding a methionine (i.e., AUG). The presence of such codons results either in the formation of a fusion protein (if the AUG codon is in the same reading frame as the desired receptor molecule encoding DNA sequence) or a frame-shift mutation (if the AUG codon is not in the same reading frame as the desired receptor molecule encoding sequence).

The expression of the receptor molecule can also be accomplished in procaryotic cells. Preferred prokaryotic hosts include bacteria such as *E. coli*, Bacillus, Streptomyces, Pseudomonas, Salmonella, Serratia, etc. The most preferred prokaryotic host is *E. coli*. Bacterial hosts of particular interest include *E. coli* K12 strain 294 (ATCC 31446), *E. coli* X1776 (ATCC 31537), *E. coli* W3110 (F−, lambda−, prototrophic (ATCC 27325)), and other enterobacteria (such as *Salmonella typhimurium* or *Serratia marcescens*), and various Pseudomonas species. The prokaryotic host must be compatible with the replicon and control sequences in the expression plasmid.

To express the desired receptor molecule in a prokaryotic cell (such as, for example, *E. coli, B. subtilis,* Pseudomonas, Streptomyces, etc.), it is necessary to operably link the desired receptor molecule encoding sequence to a functional prokaryotic promoter. Such promoters may be either constitutive or, more preferably, regulatable (i.e., inducible or derepressible). Examples of constitutive promoters include the int promoter of bacteriophage λ, and the bla promoter of the β-lactamase gene of pBR322, etc. Examples of inducible prokaryotic promoters include the major right and left promoters of bacteriophage λ ($P_L$ and $P_R$), the trp, recA, lacZ, lacI, gal, and tac promoters of *E. coli,* the α-amylase (Ulmanen, I., et al., *J. Bacteriol.* 162:176–182 (1985)), the σ-28-specific promoters of *B. subtilis* (Gilman, M. Z., et al., *Gene* 32:11–20 (1984)), the promoters of the bacteriophages of Bacillus (Gryczan, T. J., In: *The Molecular Biology of the Bacilli,* Academic Press, Inc., NY (1982)), and Streptomyces promoters (Ward, J. M., et al., *Mol. Gen. Genet.* 203:468–478 (1986)). Prokaryotic promoters are reviewed by Glick, B. R., (*J. Ind. Microbiol.* 1:277–282 (1987)); Cenatiempo, Y. (*Biochimie* 68:505–516 (1986)); and Gottesman, S. (*Ann. Rev. Genet.* 18:415–442 (1984)).

Proper expression in a prokaryotic cell also requires the presence of a ribosome binding site upstream from the gene-encoding sequence. Such ribosome binding sites are disclosed, for example, by Gold, L., et al. (*Ann. Rev. Microbiol.* 35:365–404 (1981)).

The desired receptor molecule encoding sequence and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the desired receptor molecule may occur through the transient expression of the introduced sequence. Alternatively, permanent expression may occur through the integration of the introduced sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may complement an auxotrophy in the host (such as leu2, or ura3, which are common yeast auxotrophic markers), biocide resistance, e.g., antibiotics, or heavy metals, such as copper, or the like. The selectable marker gene can either be directly linked to the DNA gene sequences to be expressed, or introduced into the same cell by co-transfection.

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Any of a series of yeast gene expression systems can be utilized. Examples of such expression vectors include the yeast 2-micron circle, the expression plasmids YEP13, YCP and YRP, etc., or their derivatives. Such plasmids are well known in the art (Botstein, D., et al., *Miami Wntr. Symp.* 19:265–274 (1982); Broach, J. R., In: *The Molecular Biology of the Yeast Saccharomyces: Life Cycle and Inheritance,* Cold Spring Harbor Laboratory, Cold Spring Harbor, N.Y., p. 445–470 (1981); Broach, J. R., *Cell* 28:203–204 (1982)).

For a mammalian host, several possible vector systems are available for expression. One class of vectors utilize DNA elements which provide autonomously replicating extra-chromosomal plasmids, derived from animal viruses such as bovine papilloma virus, polyoma virus, adenovirus, or SV40 virus. A second class of vectors relies upon the integration of the desired gene sequences into the host chromosome. Cells which have stably integrated the introduced DNA into their chromosomes may be selected by also introducing one or more markers which allow selection of host cells which contain the expression vector. The marker may provide for prototropy to an auxotrophic host, biocide resistance, e.g., antibiotics, or heavy metals, such as copper or the like. The selectable marker gene can either be directly linked to the DNA sequences to be expressed, or introduced into the same cell by co-transformation. Additional elements may also be needed for optimal synthesis of mRNA. These elements may include splice signals, as well as transcription promoters, enhancers, and termination signals. The cDNA expression vectors incorporating such elements include those described by Okayama, H., *Mol. Cell. Biol.* 3:280 (1983), and others.

Preferred prokaryotic vectors include plasmids such as those capable of replication in *E. coli* such as, for example, pBR322, ColE1, pSC101, pACYC 184, πVX. Such plasmids are, for example, disclosed by Maniatis, T., et al. (In: *Molecular Cloning, A Laboratory Manual,* Cold Spring Harbor Press, Cold Spring Harbor, N.Y. (1982)). Bacillus plasmids include pC194, pC221, pT127, etc. Such plasmids are disclosed by Gryczan, T. (In: *The Molecular Biology of the Bacilli,* Academic Press, NY (1982), pp. 307–329). Suitable Streptomyces plasmids include pIJ101 (Kendall, K. J., et al., *J. Bacteriol.* 169:4177–4183 (1987)), and Streptomyces bacteriophages such as φC31 (Chater, K. F., et al., In: *Sixth International Symposium on Actinomycetales Biology,* Akademiai Kaido, Budapest, Hungary (1986), pp. 45–54). Pseudomonas plasmids are reviewed by John, J. F., et al. (*Rev. Infect. Dis.* 8:693–704 (1986)), and Izaki, K. (*Jpn, J. Bacteriol.* 33:729–742 (1978)).

Once the vector or DNA sequence containing the constructs has been prepared for expression, the DNA constructs may be introduced into an appropriate host. Various techniques may be employed, such as protoplast fusion, calcium phosphate precipitation, electroporation or other conventional techniques. After the fusion, the cells are grown in media and screened for appropriate activities. Expression of the sequence results in the production of the receptor molecule.

Covalent modifications of the receptor molecules of the present invention are included within the scope of this invention. Variant receptor molecule fragments may be conveniently prepared by in vitro synthesis. Such modifications may be introduced into the molecule by reacting targeted amino acid residues of the purified or crude protein with an organic derivatizing agent that is capable of reacting with selected side chains or terminal residues. The resulting covalent derivatives are useful in programs directed at identifying residues important for biological activity.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β -(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Parabromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylissurea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N═C═N—R') such as 1-cyclohexyl-3-(2-morpholinyl-(4-ethyl) carbodiimide or 1-ethyl-3 (4 azonia 4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking the receptor molecule to a water-insoluble support matrix or surface. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photo-activatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or theonyl residues, methylation of the α-amino groups of lysine, arginine, and histidine side chains (T. E. Creighton, *Proteins: Structure and Molecule Properties*, W. H. Freeman & Co., San Francisco, pp. 79–86 (1983)), acetylation of the N-terminal amine, and, in some instances, amidation of the C-terminal carboxyl groups.

Amino acid sequence variants of the receptor molecule can also be prepared by mutations in the DNA. Such variants include, for example, deletions from, or insertions or substitutions of, residues within the amino acid sequence shown, for example, in FIG. 1B. Any combination of deletion, insertion, and substitution may also be made to arrive at the final construct, provided that the final construct possesses the desired activity. Obviously, the mutations that will be made in the DNA encoding the variant must not place the sequence out of reading frame and preferably will not create complementary regions that could produce secondary mRNA structure (see EP Patent Application Publication No. 75,444).

At the genetic level, these variants ordinarily are prepared by site-directed mutagenesis of nucleotides in the DNA encoding the receptor molecule, cleavage of the DNA molecule with an appropriate endonuclease, or removal of terminal DNA sequences using an exonuclease, thereby producing DNA encoding the variant, and thereafter expressing the DNA in recombinant cell culture. The variants typically exhibit the same IL-2 binding activity as the naturally occurring analog.

While the site for introducing an amino acid sequence variation is predetermined, the mutation per se need not be predetermined. For example, to optimize the performance of a mutation at a given site, random mutagenesis may be conducted at the target codon or region and the expressed receptor molecule variants screened for the optimal combination of desired activity. Techniques for making substitution mutations at predetermined sites in DNA having a known sequence are well known, for example, site-specific mutagenesis.

Preparation of a receptor molecule variant in accordance herewith may be achieved by site-specific mutagenesis of DNA that encodes an earlier prepared variant or a nonvariant version of the protein. Site-specific mutagenesis allows the production of receptor molecule variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., *DNA* 2:183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981), the disclosure of which is incorporated herein by reference. These phage are readily commercially available and their use is generally well known to those skilled in the art. Alternatively, plasmid vectors that contain a single-stranded phage origin of replication (Veira et al., *Meth. Enzymol.* 153:3 (1987)) may be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci. (USA)* 75:5765 (1978). This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bears the desired mutation. This heteroduplex vector is then used to transform appropriate cells such as JM101 cells and clones are selected that include recombinant vectors bearing the mutated sequence arrangement.

After such a clone is selected, the mutated protein region may be removed and placed in an appropriate vector for protein production, generally an expression vector of the type that may be employed for transformation of an appropriate host.

Amino acid sequence insertions include amino and/or carboxyl-terminal fusions of from one residue to polypeptides of essentially unrestricted length, as well as intrasequence insertions of single or multiple amino acid residues. Intrasequence insertions (i.e., insertions within the complete receptor molecule sequence) may range generally from about 1 to 10 residues, more preferably 1 to 5. An example of a terminal insertion includes a fusion of a signal sequence, whether heterologous or homologous to the host cell, to the N-terminus of the receptor molecule to facilitate the secretion of mature receptor molecule from recombinant hosts.

The third group of variants are those in which at least one amino acid residue in the receptor molecule, and preferably, only one, has been removed and a different residue inserted in its place. Such substitutions preferably are made in accordance with the following Table 1 when it is desired to modulate finely the characteristics of a receptor molecule.

TABLE 1

| Original Residue | Exemplary Substitutions |
|---|---|
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Substantial changes in functional or immunological identity are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Most deletions and insertions, and substitutions in particular, are not expected to produce radical changes in the characteristics of the receptor molecule. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the native receptor molecule-encoding nucleic acid, expression of the variant nucleic acid in recombinant cell culture, and, optionally, purification from the cell culture, for example, by immunoaffinity adsorption on a polyclonal anti-receptor molecule column (to absorb the variant by binding it to at least one remaining immune epitope).

The activity of the cell lysate or purified receptor molecule variant is then screened in a suitable screening assay for the desired characteristic. For example, a change in the binding character of the receptor molecule, such as affinity for IL-2, is measured by a competitive type immunoassay. Changes in immunomodulation activity are measured by the appropriate assay. Modifications of such protein properties as redox or thermal stability, hydrophobicity, susceptibility to proteolytic degradation or the tendency to aggregate with carriers or into multimers are assayed by methods well known to the ordinarily skilled artisan.

One of ordinary skill in the art can obtain the desired protein in substantially pure form from the culture by using standard techniques such extraction, precipitation, chromatography, affinity chromatography, electrophoresis, size exclusion chromatography, and the like.

The substantially pure protein may be used as an antigen for preparing monoclonal antibodies. Thus, hybridomas capable of secreting a monoclonal antibody having a specific affinity to the IL-2R$\beta$ chain or a desired fragment thereof may be prepared by immunizing a non-human animal with recombinant IL-2R$\beta$ or a portion thereof, removing spleen cells with non-immunoglobulin secreting myeloma cells, and selecting from the resulting hybridomas a cell line which produces a monoclonal antibody having the desired binding specificity and, if desired, subsequently sub-cloning said hybridoma.

The techniques for preparing hybridomas and obtaining monoclonal antibodies in pure form therefrom are well-known and by way of example are described in European Patent Application, Publication No. 0168745, the disclosure of which is fully incorporated by reference herein.

Antibodies in accordance with the invention are useful, e.g., for diagnostic purposes and also for therapy animals by immune suppression or activation. As mentioned above, such antibodies may be raised using substantially pure recombinant protein in accordance with the invention or by transfecting the cDNA of the invention, obtaining cells expressing large amounts of the receptor and using such cells to obtain the antibodies.

The availability of monoclonal antibodies to specific sub-portions of the IL-2R$\beta$ chain enables identification of epitopes of the receptor chain and thus allows for control of the activity of the receptor using suitable monoclonal antibodies or other peptides or peptidomimetic or protein analogue substances.

In addition to the above-described functional derivatives of IL-2R$\beta$, other agents which may be used in accordance of the present invention in the therapy of animals include antibodies to IL-2R$\beta$, and anti-idiotypic antibodies to anti-IL-2R$\beta$ antibodies.

Both polyclonal and monoclonal antibodies may be employed in accordance with the present invention. Of special interest to the present invention are antibodies to IL-2R$\beta$ (or their functional derivatives), which are produced in humans, or are "humanized" (i.e. non-immunogenic in a human) by recombinant or other technology. Humanized antibodies may be produced, for example, by replacing an immunogenic portion of an antibody with a corresponding, but non-immunogenic portion (i.e. chimeric antibodies) (Robinson, R. R. et al., International Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., *Science* 240:1041–1043 (1988); Liu, A. Y. et al., *Proc. Natl. Acad. Sci. USA* 84:3439–3443 (1987); Liu, A. Y. et al., *J. Immunol.* 139:3521–3526 (1987); Sun, L. K. et al., *Proc. Natl. Acad. Sci. USA* 84:214–218 (1987); Nishimura, Y. et al., *Canc. Res.* 47:999–1005 (1987); Wood, C. R. et al., *Nature* 314:446–449 (1985)); Shaw et al., *J. Natl. Cancer Inst.* 80:1553–1559 (1988).

General reviews of "humanized" chimeric antibodies are provided by Morrison, S. L. (*Science*, 229:1202–1207 (1985)) and by Oi, V. T. et al., *BioTechniques* 4:214 (1986)).

Suitable "humanized" antibodies can be alternatively produced by CDR or CEA substitution (Jones, P. T. et al., *Nature* 321:552–525 (1986); Verhoeyan et al., *Science* 239:1534 (1988); Beidler, C. B. et al., *J. Immunol.* 141:4053–4060 (1988)).

Anti-idiotypic antibodies of interest to the present invention are capable of binding to IL-2 in competition with (or to the exclusion of) IL-2R$\beta$. Such antibodies can be obtained, for example, by raising antibody to an anti-IL-2R$\beta$ antibody, and then screening the antibody for the ability to bind IL-2.

By the term "substantially pure" is intended that the protein is free of the impurities that are naturally associated therewith. Substantial purity may be evidenced by a single band by electrophoresis.

By the term "animal" is intended all animals which may derive benefit from the administration of the IL-2R$\beta$ proteins, and IL-2R$\beta$ fragments of the invention. Foremost among such animals are humans, however, the invention is not intended to be so limited.

As indicated above, the present invention envisages soluble forms of IL-2R$\beta$ chain and of soluble IL-2 receptor. Soluble forms include those coded for by the partial cDNA sequences coding for the extracellular part of IL-2R$\beta$ or subparts thereof as described above. If desired both IL-2R$\beta$ chain and $\alpha$-chain may be produced simultaneously.

By the term "soluble" is intended that the IL-2R$\beta$ fragment is soluble in aqueous solutions which include, but are not limited to, detergent-free aqueous buffers and body fluids such as blood, plasma and serum.

The dose ranges for the administration of the IL-2$\beta$ proteins and fragments thereof as well as antibodies thereto may be determined by those of ordinary skill in the art without undue experimentation. In general, appropriate dosages are those which are large enough to produce the desired effect, for example, blocking the binding of endogenous IL-2 to its natural receptor. The dosage should not be so large as to cause adverse side effects, such as unwanted cross-reactions, anaphylactic reactions, and the like. Generally, the dosage will vary with the age, condition, sex and extent of disease in the patient, counter indications, if any, immune tolerance and other such variables, to be adjusted by the individual physician. The IL-2$\beta$ proteins and fragments thereof can be administered parenterally by injection or by gradual perfusion over time. They can be administered intravenously, intraperitoneally, intramusculary, or subcutaneously.

Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, anti-oxidants, chelating agents, inert gases and the like. See, generally, *Remington's Pharmaceutical Science,* 16th Ed., Mack Eds., 1980.

The invention also relates to a method for preparing a medicament or pharmaceutical composition comprising the IL-2β proteins and fragments thereof of the invention.

The detection and quantitation of antigenic substances and biological samples frequently utilizes immunoassay techniques. These techniques are based upon the formation of the complex between the antigenic substance, e.g., IL-2 being assayed, and another member of the complex, e.g., IL-2Rβ proteins and fragments thereof, which may be detectably labeled. In the present invention, the IL-2Rβ proteins and fragments thereof may be labeled with any conventional label.

Thus, the IL-2Rβ proteins and fragments thereof can also be used in an assay for IL-2 in a biological sample by contacting a sample, derived from an animal suspected of containing IL-2 or which has been treated with exogenous IL-2, with the IL-2Rβ proteins or fragment thereof, and detecting whether a complex has formed.

For example, a biological sample may be treated with nitrocellulose, or other solid support which is capable of immobilizing soluble protein as disclosed above. The support may then be washed with suitable buffers followed by treatment with IL-2Rβ proteins or fragment thereof, any of which may be detectably labeled. The solid phase support may then be washed with a buffer a second time to remove unbound protein and the label detected.

In carrying out the assay of the present invention on a sample containing IL-2, the process comprises:

a) contacting a sample suspected of containing IL-2 with a solid support to effect immobilization of IL-2;

b) contacting said solid support with the detectably labeled IL-2Rβ protein or fragment thereof which binds to IL-2;

c) incubating said detectably labeled molecule with said support for a sufficient amount of time to allow the detectably labelled molecule to bind to the immobilized IL-2;

d) separating the solid phase support from the incubation mixture obtained in step c); and e) detecting the bound detectably labeled molecule and thereby detecting and quantifying IL-2.

Alternatively, the detectably labeled IL-2Rβ protein or fragment thereof—IL-2 complex in a sample may be separated from a reaction mixture by contacting the complex with an immobilized antibody or protein which is specific for the IL-2Rβ protein or fragment thereof. Such anti-IL-2Rβ protein or fragment thereof antibodies may be monoclonal or polyclonal. The solid support may then be washed with suitable buffers to give an immobilized complex. The label may then be detected to give a measure of IL-2Rβ or fragment thereof and, thereby, the amount of IL-2.

This aspect of the invention relates to a method for detecting IL-2 in a sample comprising:

(a) contacting a sample suspected of containing IL-2 with IL-2Rβ or fragment thereof that binds to IL-2, and (b) detecting whether a complex is formed.

Of course, the specific concentrations of detectably labeled IL-2Rβ or fragment thereof, the temperature and time of incubation, as well as other assay conditions may be varied, depending on various factors including the concentration of IL-2 in the sample, the nature of the sample, and the like. Those skilled in the art will be able to determine operative and optimal assay conditions for each determination by employing routine experimentation.

Other such steps as washing, stirring, shaking, filtering and the like may be added to the assays as is necessary for the particular situation.

One of the ways in which the IL-2Rβ or fragment thereof can be detectably labeled is by linking the same to an enzyme. This enzyme, in turn, when later exposed to its substrate, will catalyze the formation of a product which can be detected as, for example, by spectrophotometric, fluorometric or by visual means. Enzymes which can be used to detectably label the IL-2Rβ or fragment thereof of the present invention include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase.

The IL-2Rβ or fragment thereof of present invention may also be labeled with a radioactive isotope which can be determined by such means as the use of a gamma counter or a scintillation counter or by autoradiography. Isotopes which are particularly useful for the purpose of the present invention are: $^{3}H$, $^{125}I$, $^{131}I$, $^{32}P$, $^{35}S$, $^{14}C$, $^{51}Cr$, $^{36}Cl$, $^{57}Co$, $^{58}Co$, $^{59}Fe$ and $^{75}Se$.

It is also possible to label the IL-2Rβ or fragment thereof with a fluorescent compound. When the fluorescently labeled immunoglobulin-like molecule is exposed to light of the proper wave length, its presence can then be detected due to the fluorescence of the dye. Among the most commonly used fluorescent labelling compounds are fluorescein isothiocyanate, rhodamine, phycoerythrin, phycocyanin, allophycocyanin, o-phthaldehyde and fluorescamine.

The IL-2Rβ or fragment thereof of the invention can also be detectably labeled using fluorescence emitting metals such as $^{152}Eu$, or others of the lanthanide series. These metals can be attached to the IL-2Rβ or fragment thereof, using such metal chelating groups as diethylenetriaminepentaacetic acid (DTPA) or ethylenediaminetetraacetic acid (EDTA).

The IL-2Rβ or fragment thereof of the present invention also can be detectably labeled by coupling it to a chemiluminescent compound. The presence of the chemiluminescent-tagged IL-2Rβ or fragment thereof is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the IL-2Rβ or fragment thereof of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the IL-2Rβ or fragment thereof may be accomplished by a scintillation counter, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection may also be accomplished by visual comparison of the extent of enzymatic reaction of a substrate in comparison with similarly prepared standards.

The assay of the present invention is ideally suited for the preparation of a kit. Such a kit may comprise a carrier means being compartmentalized to receive in close confinement therewith one or more container means such as vials, tubes and the like, each of said container means comprising the separate elements of the immunoassay. For example, there may be a container means containing a solid phase support, and further container means containing the detectably labeled IL-2Rβ or fragment thereof. Further container means may contain standard solutions comprising serial dilutions of analytes such as IL-2 to be detected. The standard solutions of these analytes may be used to prepare a standard curve with the concentration of IL-2 plotted on the abscissa and the detection signal on the ordinate. The results obtained from a sample containing IL-2 may be interpolated from such a plot to give the concentration of IL-2.

The following examples are illustrative, but not limiting the method and composition of the present invention. Other suitable modifications and adaptations which are obvious to those skilled in the art are within the spirit and scope of this invention.

EXAMPLE 1

Isolation and Analysis of the cDNA Clones Coding for Human IL-2Rβ Chain

In isolating the cDNA clones, an expression cloning strategy was applied by using the monoclonal antibodies, Mike-β1 and Mik-β2, both of which have been raised against the IL-2Rβ chain found on the human leukemic cell line YT (Yodoi, J., et al., *J. Immunol.* 134:1623 (1985)).

The monoclonal antibodies Mik-β1 and Mik-β2 are both deposited at Fermentation Research Institute, Agency of Industrial Science and Technology, Japan. The deposit numbers for Mik-β1 and Mik-β2 are 10453 and 10454 (1988), respectively; they are also described in Japanese Patent Application No. 298742 (1988).

A few sets of cDNA libraries were prepared by using the poly(A)+-RNA from YT cells according to standard procedures. cDNA libraries were prepared with cDM8 vector according to published procedures (Seed, B., et al., *Proc. Natl. Acad. Sci. USA* 84:3365 (1987); Seed, B., *Nature* 328:840 (1987)), except using random primer (Amersham) or oligo (dT) primer as mentioned below. The plasmid DNA representing $5.6 \times 10^6$ independent colonies was prepared by the standard procedure and one mg of DNA was used for the first DNA transfection. The DNA was divided into 100 tubes (therefore each tube contained 10 μg of DNA) and they were each transfected into $3.5 \times 10^5$ monkey COS cells in a tissue culture dish (60 mm polystyrene dish, Corning). The transfection was done using the standard DEAE dextran procedures. The transfected COS cells were then treated with the cocktail of Mik-β1 and -β2 antibodies (400-fold diluted ascites for each antibody) and subjected to the standard panning procedure. The dish used for the panning was FALCON 60 mm disk, coated with anti-mouse IgG as described previously (Seed, B., et al., *Proc. Natl. Acad. Sci. USA* 84:3365 (1987); Seed, B., *Nature* 328:840 (1987)). In this first round of panning, 100 IgG-coated dishes were used. After the panning, Hirt extract was prepared by the standard procedure (Seed, B., et al., *Proc. Natl. Acad. Sci. USA* 84:3365 (1987); Seed, B., et al., *Nature* 328:840 (1987)) and the recovered plasmids were introduced into *E. coli* by the method described in Seed, B., et al., *Proc. Natl. Acad. Sci. USA* 84:3365 (1987), and Seed, B., et al., *Nature* 328:840 (1987). By this procedure, $3.7 \times 10^6$ colonies were obtained. Those bacterial colonies were fused with COS cells by the standard protoplast fusion procedures (Seed, B., et al., *Proc. Natl. Acad. Sci. USA* 84:3365 (1987); Seed, B., et al., *Nature* 328:840 (1987)). In these fusion experiments, 26 Corning dishes each containing $5 \times 10^5$ COS cells were used. After the fusion, the COS cells were subjected to panning as described above, and Hirt extract was prepared. 32,000 bacterial colonies were obtained from the Hirt extract. The fusion, panning procedures were repeated again and 32,000 bacterial colonies were obtained from the subsequent Hirt extract. The same procedures were repeated once again, obtaining 28,000 bacterial colonies (in the meantime, there should be a dramatic enrichment of the objective clones). The same procedures were repeated once again and 6,000 colonies were obtained. From these colonies, 30 colonies were picked up randomly and the cDNA inserts were analyzed. Of them, only 7 colonies contained plasmids from which cDNA inserts can be excised by restriction enzyme XhoI. The vector derived XhoI sites were located at both sides of the cDNA and all other plasmids had lost such cleavage sites due to the DNA rearrangements; in fact, all of them were much smaller in size than the original vector. Thus they were considered to be non-specific products. On the other hand, all of the 7 colonies were derived from the same mRNA, as confirmed by the conventional restriction enzyme cleavage analysis and DNA blot analysis. Of them, one plasmid, termed pIL-2Rβ30, contained longer cDNA than the other 6 plasmids which turned out to be identical to each other (designated pIL-2Rβ9).

In this procedure, two independent cDNA clones, pIL-2Rβ9 and pIL-2β30, were isolated; each of the expression products specifically reacted with the antibodies. The two clones contained cDNA inserts of 1.3 Kb and 2.3 Kb, respectively, and cross-hybridized with each other. Subsequent sequence analysis of the cDNAs revealed that they represent the same mRNA. In fact, RNA blotting analysis revealed that the mRNA is approximately 4 Kb in size (see below). Subsequently, we screened other YT cDNA libraries by using the cloned cDNAs as probes, and several independent cDNA clones which together cover the entire mRNA for the IL-2Rβ chain were isolated. Thus, pIL-2Rβ6 and pIL-2Rβ19 were obtained by screening the cDNA libraries with the pIL-2Rβ9 cDNA insert in the probe.

The above-mentioned plasmids containing cDNA coding for human IL-2Rβ sequences have been deposited in *E. coli* strain MC 1061/P3 on Mar. 2, 1989 at the Fermentation Research Institute according to the Budapest Treaty under the following accession numbers:

| Plasmid | Accession No. |
| --- | --- |
| pIL-2Rβ6 | FERM BP-2312 |
| pIL-2Rβ9 | FERM BP-2313 |
| pIL-2Rβ19 | FERM BP-2314 |
| pIL-2Rβ30 | FERM BP-2315 |

The complete nucleotide sequences of four of the cloned cDNAs were determined and are depicted in FIG. 1B.

FIGS. 1A and 1B show the structure of the human IL-2Rβ chain cDNA. FIG. 1A is a schematic representation of the mRNA as deduced from the cloned cDNAs. Dotted, hatched, open and closed rectangles representing respectively the signal sequence, the extracellular, the transmembrane and the cytoplasmic regions of the mRNA are shown below. FIG. 1B shows the nucleotide and amino acid sequences of the human IL-2Rβ chain cDNA. The sequence was deduced following the complete DNA sequence analysis of the above-described cDNA clones. Nucleotides are numbered on the right margin and amino acids are numbered on the left margin. Clones pIL-2Rβ19 and pIL-2Rβ6 each contained G-A mutation at nucleotide residues 425 and 1531, respectively. Thus pIL-2Rβ6 cDNA acquired a TAG triplet in the cytoplasmic region. It is thought to be an error in reverse transcription, since all other clones, pIL-2Rβ30, pIL-2β19 and pIL-2Rβ16, have a TGG triplet at that position. The first underlined 26 amino acid residues represent the signal sequence as predicted by the consensus sequence (Perlman, D., et al., *J. Mol. Biol.* 167:391 (1983); von Heijne, G., *Nucleic Acids Res.* 14:4683 (1986)). The 25 transmembrane amino acid residues are marked with a thick underlining. The cysteine residues are boxed. The potential N-glycosylation sites are underlined twice. The possible poly-adenylation signals are shown by open rectangle. In summary, RNA was prepared from the NK-like human lymphoid cell line, YT, and cDNA libraries were prepared with CDM8 vector according to published procedures (Seed, B., et al., *Proc. Natl. Acad. Sci. USA* 84:3365 (1987); Seed, B., *Nature* 328:840 (1987)), except using either random primers (Amersham) (for pIL-2Rβ6, 9 and 30) or oligo (dT) primers (for pIL-2Rβ19). Screening of the cDNA libraries by a cocktail of anti-IL-2Rβ monoclonal antibodies, Mik-β1 and Mik-β2, was carried out as described previously (Seed, B., et al., *Proc. Natl. Acad. Sci. USA* 84:3365 (1987); Seed, B., *Nature* 328:840 (1987)). Nucleotide sequences were determined by a combination of dideoxy chain termination and chemical cleavage methods.

As shown in FIG. 1B, the cDNA contains a large open reading frame that encodes a protein consisting of 551 amino acids. No significant homology with other known proteins was found in the Protein Sequence Database (National Biomedical Research Foundation, Washington, D.C.) or with sequences published more recently. Unlike many of other cytokine receptors, it appears that IL-2Rα and IL-2Rβ chains do not belong to the immunoglobulin superfamily. From the deduced structure of the protein, the N-terminal 26 amino acids is considered to represent the signal sequence. Thus the mature form of the IL-2Rβ chain consists of 525 amino acids with a calculated M.W. of 58,358. As shown in FIG. 1A, the receptor molecule consists of an extracellular region consisting of 214 amino acids. This region contains 8 cysteine residues of which 5 residues are found in the N-terminal half and they are interspaced rather periodically by 9–12 amino acids. It is likely that disulfide linkages between the cysteine residues impart a stable configuration for ligand binding. In fact, abundance of cysteine residues seems to be one of the common features of the ligand binding domain of many receptors (Ullrich, A., et al., *Nature* 309:418 (1984); Ullrich, A., et al., *Nature* 313:756 (1985); Ebina, U., et al., *Cell* 40:747 (1985)). It may be worth noting that the predicted number of amino acids (a.a.) within the extracellular region of the IL-2Rβ chain (214 a.a.) is almost comparable in number to that of the IL-2Rα chain (219 a.a.). Such size similarity may be significant in considering the conformation of the heterodimeric receptor complex that is quite unique for this receptor; as both α and β chains individually interact with distinct sites of the same IL-2 molecule (Collins, L., et al., *Proc. Natl. Acad. Sci. USA* 85:7709 (1988)).

Figure 2:
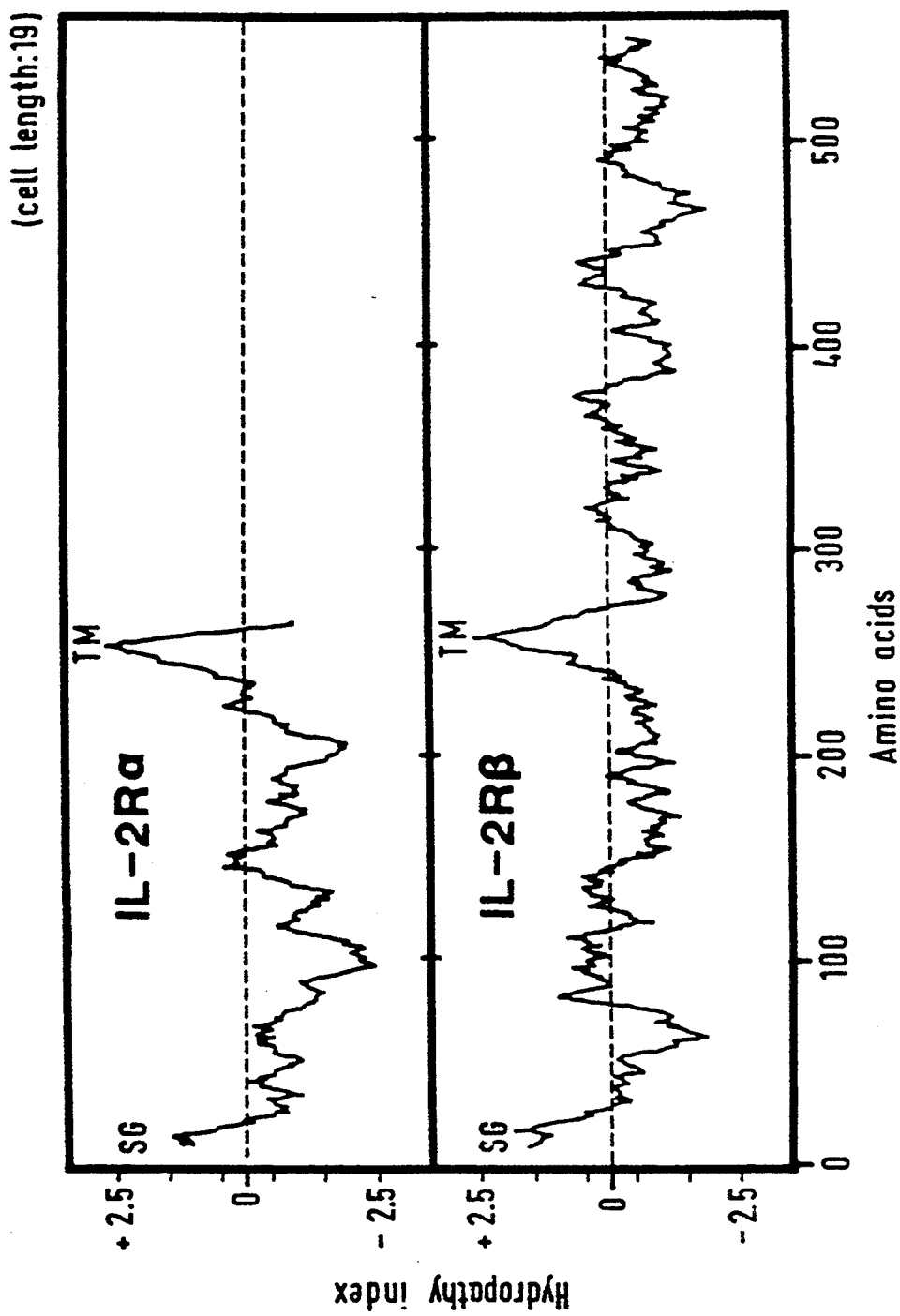
FIG. 2 is a hydropathy plot analysis of deduced human IL-2Rα and IL-2Rβ chain precursor structures.

A hydrophobic stretch of 25 amino acids spanning from the 215 to 239 amino acid residues appears to constitute the membrane spanning region of the receptor (FIGS. 1B and 2).

FIG. 2 is a hydropathy plot analysis of deduced human IL-2Rα and IL-2Rβ chain precursor structures. The analysis was carried out according to Kyte and Doolittle. SG and TM represent signal sequence and transmembrane sequence respectively.

The cytoplasmic region of the β chain consists of 286 a.a. and it is far larger than that of the α chain, which is only 13 a.a. long. The consensus sequences of tyrosine kinase (Gly-x-Gly-x-x-Gly) (Hanks, K. S., et al., *Science* 241:42 (1988)) are absent in the β chain. However, the presence of a triplet, Ala-Pro-Glu (293–295) may be noted; this has been asserted to be the consensus motif for a catalytic domain of some protein kinases (Hanks, K. S., et al., *Science* 241:42 (1988)). The possibility of the cytoplasmic region of the β chain having a protein kinase activity has yet to be tested. The primary structure of this region revealed yet another interesting feature; a rather strong bias for certain characteristic amino acids. This region is rich in proline (42/286) and serine (30/286) residues. Interestingly, the "proline rich" structure has also been demonstrated in the cytoplasmic region of CD2, a T cell membrane antigen involved in the activation pathway of T cells (Alcover, A., et al., *Immunol. Rev.* 95:5 (1987)). The proline-rich structure may impart a non-globular conformation to this region that may be important in coupling of the receptor molecule with other signal transducer(s). The predominant serine residues may be the major target for phosphorylation, which could also modulate the receptor function (Hatakeyama, M., et al., *Proc. Natl. Acad. Sci. USA* 83:9650 (1986)). In addition, the cytoplasmic region is notably biased for negatively charged amino acids. In fact, this region contains 40 such amino acids (i.e., glutamic and aspartic acids), whereas only 18 amino acids account for the positively charged residues (i.e., lysine and arginine). Such a bias is particularly notable in the middle portion (a.a. 345–390) of the cytoplasmic region. Thus, the cytoplasmic region of the β-chain may be quite acidic. Taken together, some, if not all, of these unique characteristics may be responsible in driving further the downstream signal transduction pathway(s). The receptor protein contains 5 potential sites for N-linked glycosylation (FIG. 1B), of which 4 are located in the extracellular region. Such a posttranslational modification may account for the difference between the M.W. of the estimated mature (70–75 kD) and the calculated (58 kD) protein molecules. Hydropathy plot analysis of the α and β chains revealed the presence of hydrophilic regions just adjacent to the cell membrane in both chains (FIG. 2). These regions may play a role in the non-covalent intramolecular association between the two chains.

EXAMPLE 2

Expression of Human IL-2Rβ Chain mRNA

Expression of the IL-2Rβ mRNA was examined by using the cDNA insert from pIL-2Rβ30 as the probe.

Figure 3A:
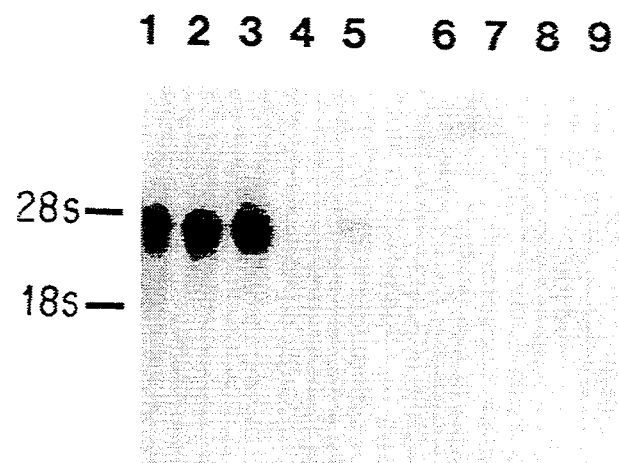
FIG. 3A illustrates the expression of human IL-2Rβ chain mRNA in different cell types.

FIG. 3a illustrates the expression of human IL-2Rβ chain mRNA in different cell types. Poly (A)+RNA (2 μg per lane) from the following cell sources was prepared and subjected to RNA blotting analysis using the XhoI-digested human IL-2Rβ chain cDNA fragment derived from pIL-2Rβ30 as a probe following standard procedures (Hatakeyama, M., et al., Nature 318:467 (1985); Hatakeyama, M., et al., J. Exp. Med. 166:362 (1987); Kondo, S., et al., Nature 327:64 (1987); Hatakeyama, M., et al., Proc. Natl. Acad. Sci. USA 83:9650 (1986)). Lane 1, YT; lane 2, Hut102 (HTLV-1 transformed human T cell line); lane 3, MT-2 (HTLV-1 transformed human T cell line); lane 4, ARH-77 (multiple myeloma line); lane 5, SKW6.4 (EBV-transformed human B lymphoblastoid line); lane 6, U937 (histiocytic leukemia line); lane 7, MT-1 (HTLV-1 transformed human T cell line); lane 8, Jurkat (human T leukemic line); lane 9, HeLa (human cervical carcinoma cell line).

As shown in FIG. 3a, the RNA blot analysis revealed the presence of a 4 kb mRNA, the expression of which is restricted to lymphoid cells previously identified to bear IL-2Rβ chain (i.e., YT, MT-2, Hut102, SKW6.4) (Tsudo, M., et al., Proc. Natl. Acad. Sci. USA 83:9694 (1986); Teshigawara, K., et al., J. Exp. Med. 165:223 (1987); Sharon, M., et al., Science 234:859 (1986); Robb, R. J., et al., Proc. Natl. Acad. Sci. USA 84:2002 (1987); Tsudo, M., et al., Proc. Natl. Acad. Sci. USA 84:4215 (1987); Dukovich, M., et al., Nature 327:518 (1987)). On the other hand, the mRNA expression was not detected in cells such as Jurkat, MT-1, U937, ARH-77 and HeLa cells. Essentially, the mRNA expression levels are in correlation with the IL-2Rβ chain expression levels.

Figure 3B:
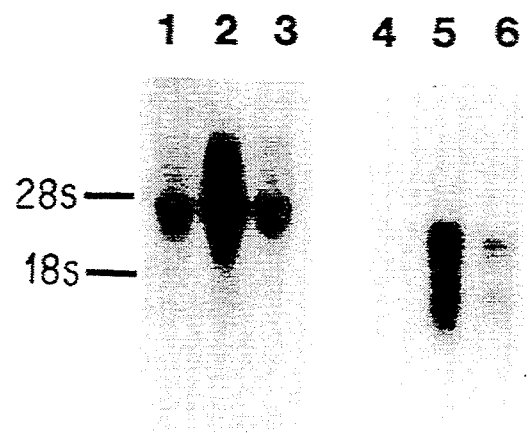
FIG. 3B illustrates the expression of IL-2Rβ and IL-2Rα mRNAs in human PBLs.

FIG. 3b illustrates the expression of IL-2Rβ and IL-2Rα mRNAs in human PBLs. Total RNA (15 μg per lane) was loaded in each lane. Lanes 1 and 4 represent unstimulated human peripheral blood lymphocytes (PBLs); lanes 2 and 5, PBLs stimulated with 5 μg/ml phytohemagglutinin (PHA) for 24 hrs; lanes 3 and 6, PBLs stimulated with 5 μg/ml PHA for 72 hrs. The RNA-blotted filter was hybridized with the IL-2Rβ probe (lanes 1–3). After dehybridization of the IL-2Rβ probe, the same filter was hybridized with the IL-2Rα probe (XbaI-BclI fragment derived from pSVIL2R-3 (Hatakeyama, M., et al., Nature 318:467 (1985)) (lanes 4–6).

Interestingly, its IL-2Rβ mRNA was detectable in the unstimulated PBLs and its expression levels increased transiently only 2.5-fold after mitogen stimulation. Based on data derived from flow cytometric analysis, it is likely that the mRNA induction patterns differ between the different lymphocyte populations. This expression pattern is quite different from that of the IL-2Rα chain whose expression strictly requires mitogenic stimulation of the cells (FIG. 3b), suggesting the presence of distinct mechanisms of gene expression between the two genes.

Southern blot analysis of the genomic DNA from PBL and various cell lines including HTLV-1-transformed human T cell lines indicates that the gene is present in a single copy and is not rearranged in those cells.

EXAMPLE 3

IL-2 Binding Properties of the cDNA-encoded IL-2Rβ Chain

Next, a series of cDNA expression studies was carried out in order to examine whether the cDNA product binds IL-2 and indeed manifests the properties of the IL-2Rβ chain that have been demonstrated and/or suggested in previous studies. Two cDNA expression plasmids were constructed in which expression of the cDNA spanning the entire coding region was directed by either the mouse lck gene (Marth, J. D., et al., Cell 43:393 (1985)) promoter (pLCKRβ) or Moloney leukemia virus LTR (Mann, R., et al., Cell 33:153 (1983)) (pMLVRβ).

Expression vectors were constructed by the following procedures. pIL-2Rβ30 was digested with HindIII (the cleavage site is located within the polylinker regions of CDM8) and, after fill-in of both ends, a BamHI linker was attached and religated. The resulting plasmid was then digested with BamHI and the 1.8 kb DNA fragment which contains the entire coding sequence for the β chain was introduced into BamHI-cleaved p1013 vector containing the mouse lck promoter to construct pLCKRβ. The BamHI-digested cDNA fragment was also introduced into a retrovirus vector, pZipSV(X) (Mann, R., et al., Cell 33:153 (1983)), to construct pMLVRβ. The human IL-2Rα expression vector, pSVIL2Rneo, was obtained from pSVIL2R-3 (Hatakeyama, M., et al., Nature 318:467 (1985)) by replacing the Eco-gypt gene with the neo-resistance gene.

The plasmid pLCKRβ was introduced into the mouse T lymphoma EL-4 and the human T cell leukemia Jurkat lines, both of which are known to be devoid of surface molecules that bind human IL-2.

Transfection of the expression plasmids into Jurkat and EL-4 cells was carried out by electroporation. Transfected cells were selected in the RPMI1640 medium containing 10% fetal calf serum (FCS) and G418 (1 mg/ml for EL-4 and 1.5 mg/ml for Jurkat). To obtain cells expressing cDNAs for human IL-2Rα and IL-2Rβ chains simultaneously, a Jurkat-derived clone Ja-5, transfected with pSVIL2Rneo, was co-transfected with pLCKRβ and a plasmid containing the hygromycin-resistance gene, pHgy. The transfected cells were selected with 200 μg/ml hygromycin. Transfection of pMLVRβ into 2 cells was carried out by calcium-phosphate method as described previously (Hatakeyama, M., et al., Nature 318:467 (1985)) and the cells were selected by 700 μg/ml of G418. For flow cytometric analysis, $5 \times 10^5$ cells were treated with antibody (1:500 dilution of ascites) at 4° C. for 30 min. After washing, cells were stained with fluorescein-conjugated goat anti-mouse IgG.

The stained cells were analyzed on a FACS440 flow cytometer (Beckton Dickinson). The $^{125}$I-IL-2 binding assay and Schatchard plot analysis were carried out as described previously (Tsudo, M., et al., Proc. Natl. Acad. Sci. USA 83:9694 (1986); Teshigawara, K., et al., J. Exp. Med. 165:223 (1987)).

FIG. 4A illustrates the expression of human IL-2Rα and/or IL-2Rβ chain cDNAs by means of cell surface staining patterns of human IL-2Rα and/or IL-2Rβ cDNA transfectants. Parental cells and various transfectant cells were separately stained with either a monoclonal anti-human IL-2Rα antibody, anti-Tac (- - -), or monoclonal anti-human IL-2Rβ antibody, Mik-β1 (—).

Dotted line ( . . . ) is a fluorescence profile of the cells stained with fluorescein-conjugated goat-anti-mouse IgG alone. Cells used were (1) ELβ-13 (and EL-4-derived clone transfected with pLCKRβ), (2) Jβ-8 (a Jurkat-derived clone transfected with pLCKRβ), (3) Jα-5 (a Jurkat-derived clone transfected with pSVIL2Rneo), (4) Jα-2 (a Jα-5-derived clone transfected with pLCKRβ), (5) Jαβ-10 (a Jα-5-derived clone transfected with pLCKRβ), and (6) Fβ-3 (a NIH3T3-derived line transfected with pMLVRβ).

Stable transformant clones expressing the cDNA product were obtained for both the EL-4 (ELβ-13) and Jurkat (Jβ-8) cells as judged by FACS analysis (FIG. 4A). In addition, we also introduced the same gene into the Jurkat transformant clone, Jα-5, which expresses the transfected, human IL-2Rα chain cDNA. Two of the resulting transformants, Jαβ-2 and Jαβ-10, were found to express both α and β chains (FIG. 4A-(4), (5)). As expected, RNA blotting analyses of the mRNA expressed in those transformants revealed that the α and β chain-specific mRNAs are derived from the transfected cDNAs but not from the endogenous genes (Alcover, A., et al., *Immunol. Rev.* 95:5 (1987)). Furthermore, in order to examine the property of the cDNA product in non-lymphoid cells, the plasmid pMLVRβ was introduced into an NIH3T3 cell-derived cell line 2 (Mann, R., et al., *Cell* 33:153 (1983)), and the resulting transformant expressing the cDNA, Fβ-3, was obtained (FIG. 4A-(6)).

The IL-2 binding studies were carried out with $^{125}$I-labeled, recombinant human IL-2.

FIG. 4B illustrates the expression of the α and β chains by means of the Scatchard plot analysis of $^{125}$I-IL-2 binding to the transfectants expressing the cloned cDNAs. Scatchard plot of the IL-2 binding data in the absence (-o-o-) or presence (-●-●-) of 1:100-diluted ascites of Mik-β1. Binding of $^{125}$I-IL-2 to ELβ-13 or Jβ-8 was completely abolished by Mik-β1. No specific IL-2 binding was observed when parental Jurkat or EL-4 cells were examined. The number of IL-2 binding sites per cell and the receptor affinity were determined by computer-assisted analysis of the IL-2 binding data. (1) ELβ-13, (2) Jβ-8, (3) Jα-5, (4) Jαβ-2, (5) Jαβ-10.

As can be seen, the EL-4-derived clone (ELβ-13) and the Jurkat-derived clone (Jβ-8), both expressing the β chain cDNA, displayed intermediate-affinity to IL-2 with estimated Kd values of 4.0 nM and 2.7 nM, respectively. The IL-2 binding to those cells was completely abolished by the Mik-β1 antibody (FIG. 4B-(1), (2)). The Jurkat-derived Jαβ-2 and Jαβ-10 clones expressing both the human IL-2Rα and IL-2Rβ cDNA displayed both high and low affinity receptors with estimated Kp values of 22 pM and 15 nM for Jαβ-2 and 19 pM and 33 nM for Jαβ-10, respectively. In contrast, the parental, Jurkat-derived Jα-5 cells expressing the α chain cDNA alone manifested exclusively low-affinity (Kd: 19.5 nM) to IL-2 (FIG. 4B-(3)). The number of the high-affinity IL-2R expressed Jαβ-2 cells and Jαβ-10 was comparable to that of expressed IL-2Rβ molecules. In addition, treatment of these cells with Mik-β1 antibody completely abolished high-affinity IL-2 binding sites from the cell surface, while retaining the expression of low-affinity IL-2R (FIG. 4B-(4), (5)). These observations demonstrate unequivocally that the cDNA-encoded IL-2Rβ molecule is directly involved in the formation of high-affinity receptor complex in association with the IL-2Rα chain. In contrast to the aforedescribed T cell transformants, the Fβ-3 cells did not display any IL-2 binding on the cell surface under same binding conditions. Interestingly the same observation was made with monkey COS cells that express the β chain, but failed to bind IL-2. Thus, the results suggest the involvement of either a cell-type specific processing mechanism(s) or an additional cellular component(s), or both for the functional IL-2Rβ chain expression.

In order to characterize further the molecular structure of reconstituted IL-2R, crosslinking experiments were performed with $^{125}$I-IL-2 and non-cleavable chemical crosslinker, dissuccinimidyl suberate (DSS).

Figure 5:
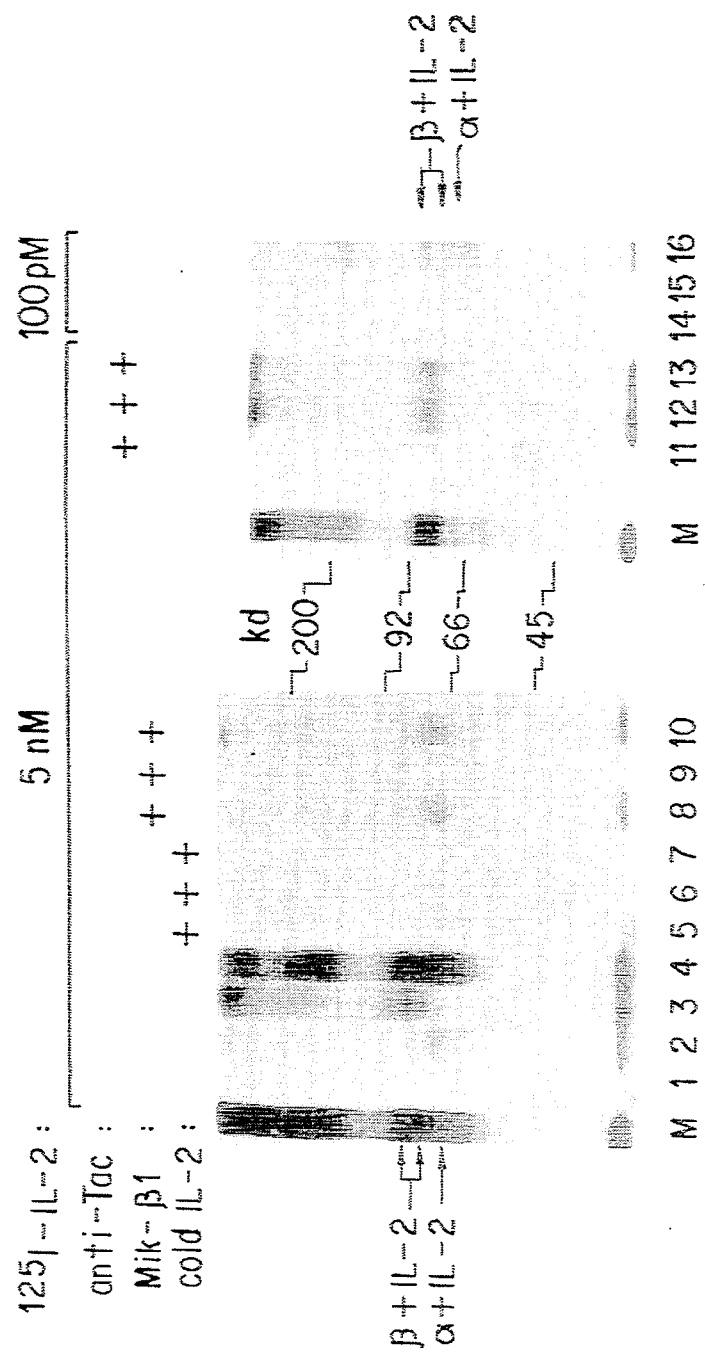
FIG. 5 illustrates the results of the affinity crosslinking studies of the IL-2R-positive transformants.
Figure 6A:
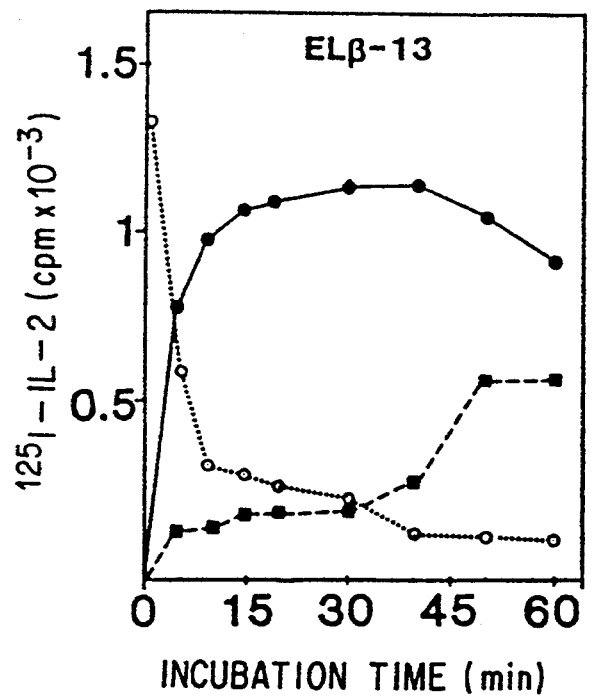
FIGS. 6A–6D illustrate IL-2 internalization via the reconstituted receptors.
Figure 6B:
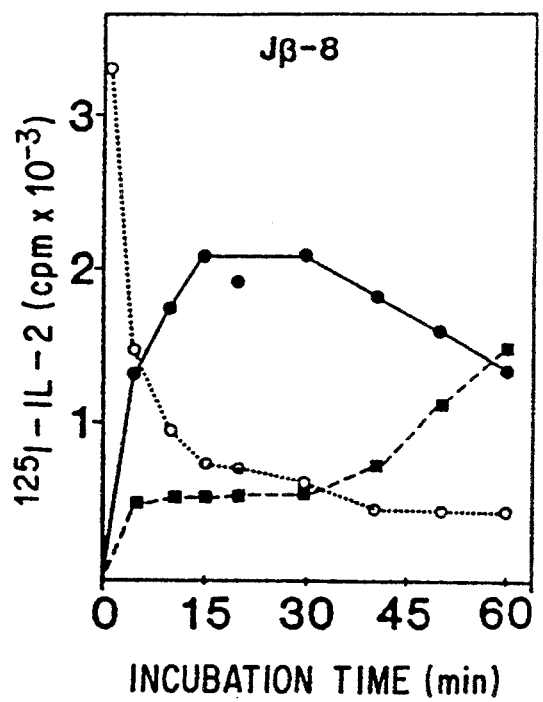
Figure 6C:
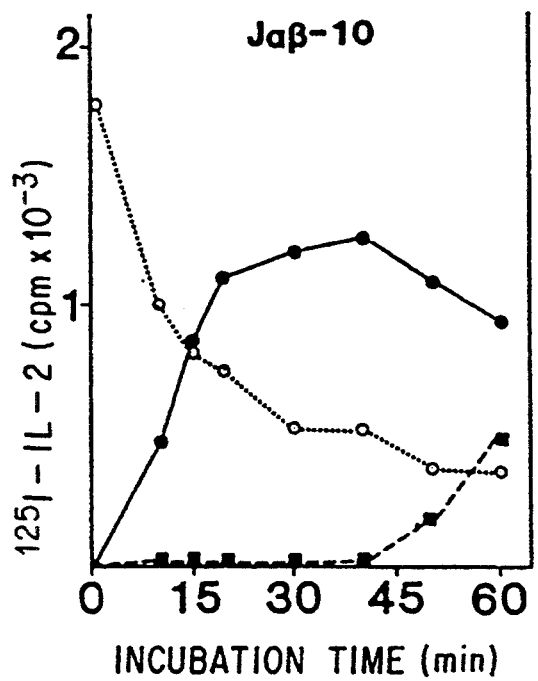
Figure 6D:
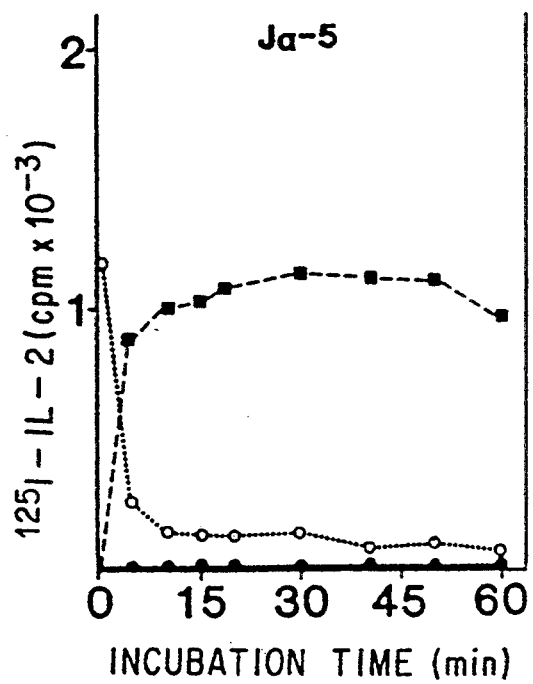

FIG. 5 illustrates the results of the affinity crosslinking studies of the IL-2R-positive transformants. Cells were incubated with 5 nM (lanes 1-13) or 100 pM (lanes 14-16) of $^{125}$I-IL-2 in the absence (lanes 1-4, 14-16) or presence of a 250-fold molar excess of unlabeled IL-2 (lanes 5-7), 500-fold molar excess of affinity column-purified Mik-β1 (lanes 8-10) or 500-fold molar excess of affinity column-purified anti-Tac (lanes 11-13). Then cells were chemically crosslinked with dissuccinimidyl suberate (DSS) as described previously (Sharon, M., et al., *Science* 234:859 (1986)). The cells were then solubilized and the supernatants were subjected to 7.5% SDS-PAGE. Cells used were: Jurkat (lane 1); Jα-5 (lanes 2, 5, 8, 11, 14); Jβ-8 (lanes 3, 6, 9, 12, 15); 5Jαβ-10 (lanes 4, 7, 10, 13, 16). YT cells crosslinked with $^{125}$I-IL-2 were used as a marker (M).

As can be seen, cells expressing only IL-2Rβ chain were crosslinked with $^{125}$I-labeled IL-2 and analyzed by SDS-PAGE, a doublet band consisting of 90 kD major and 85 kD minor was detected and its migration profile was indistinguishable from that of YT cells (see arrows in FIG. 5; Sharon, M., et al., *Science* 234:859 (1986); Robb, R. J., et al., *Proc. Natl. Acad. Sci. USA* 84:2002 (1987); Tsudo, M., et al., *Proc. Natl. Acad. Sci. USA* 84:4215 (1987); Dukovich, M., et al., *Nature* 327:518 (1987)). The appearance of the doublet is inhibited by an excess of unlabeled IL-2 or by Mik-β1. The doublet formation may be due to degradation of receptor-IL-2 complex. It is also possible that both protein products are derived by a differential post-translational modification(s). Alternatively, one of the doublet may represent a third component of the receptor complex. A broad band migrating around the position of 150 kD was also detected in the transfectant (Jαβ-10) as well as YT cells. The appearance of this band is also inhibited by either unlabeled IL-2 or Mik-β1. It may represent the ternary complex of IL-2, IL-2Rα and IL-2Rβ molecules. In a series of chemical cross-linking experiments shown in FIGS. 4A and 4B, it was demonstrated that the physicochemical properties of the receptor complex expressed on the surface of Jαβ-2 are indistinguishable from the properties of high-affinity receptor expressed on cultured T cells or PBLs (Tsudo, M., et al., *Proc. Natl. Acad. Sci. USA* 83:9694 (1986); Teshigawara, K., et al., *J. Exp. Med*, 165:223 (1987); Sharon, M., et al., *Science* 234:859 (1986); Robb, R. J., et al., *Proc. Natl. Acad. Sci USA* 84:2002 (1987); Tsudo, M., et al., *Proc. Natl. Acad. Sci. USA* 84:4215 (1987); Dukovich, M., et al., *Nature* 327:518 (1987)).

Preliminary results of experiments to determine whether the expression of the α and β chains in non-lymphoid cells results in the formation of a high-affinity receptor indicate that, when the α and β chain cDNAs are co-expressed transiently in COS cells, both chains can cross-link with $^{125}$I-IL-2 at the concentration (400 pM) in which the similarly expressed α chain alone cannot. The results may suggest the formation of the αβ heterodimeric receptor in this non-lymphoid cell line.

EXAMPLE 5

IL-2 Internationalization by Reconstituted Receptors

It has been reported that intermediate- and high-affinity IL-2 receptors can both internalize IL-2 (Robb, R. J., et al., *J. Exp. Med.* 165:1201 (1987); Sugamura, K., et al., *J. Exp. Med.* 161:1243 (1985); Saragovi, H., et al., *J. Immunol.* 141:476 (1988)). Ligand internalization is usually accompanied with the IL-2 signal transduction, suggesting this process to be essential.

FIG. 6A-6D illustrate IL-2 internalization via the reconstituted receptors. IL-2 internalization was examined according to a method described previously (Robb, R. J., et al., *J. Exp. Med.* 165:1201 (1987)). Briefly, cells ($5 \times 10^7$) were treated with $^{125}$I-IL-2 at a final concentration of 200 pM (Jαβ-10) or 5 nM (Jα-5, Jβ-8 and ELβ-13) at 0° C. for 30 min. After washing, cells were suspended with prewarmed culture medium (37° C.) and the kinetics of IL-2 internalization was examined as described previously (Robb, R. J., et al., *J. Exp. Med.* 165:1201 (1987)). (A) ELβ-13, (B) Jβ-8, (C) Jαβ-10, (D) Jα-5. (-●-●-●-), internalized IL-2; (...o...o...), cell-surface bound IL-2; (-■-■-■-■-), free IL-2.

As shown in FIGS. 6A-6D, it was examined whether the reconstituted receptors can internalize IL-2. In fact, the cells expressing IL-2Rβ chain alone, or both α and β chains are capable of internalizing IL-2 following a kinetic pattern similar to that reported for the native receptor. In contrast, the Jurkat cells expressing only IL-2Rα failed to internalize IL-2, similar to previously reported observations (Robb, R. J., et al., *J. Exp. Med.* 165:1201 (1987); Sugamura, K., et al., *J. Exp. Med.* 161:1243 (1985)). Preliminary results indicate that the growth of the cells expressing the intermediate- or high-affinity receptors is selectively inhibited by IL-2 (Hatakeyama, M., et al., *Nature* 318:467 (1985); Kyte, J., et al., *J. Mol. Biol.* 157:105 (1982)). We also have preliminary results that the β chain expressed in another host cell line functions in stimulating the cell growth in response to IL-2.

EXAMPLE 6

Cloning of Murine IL-2R Receptor β Chain

No specific antibodies to murine IL-2 receptor β-chain are known to exist. Accordingly, the screening method used for the isolation of cDNA for Hu IL-2Rβ chain was not employed.

A cDNA library was prepared using poly(A)+-RNA from Concanavalin A stimulated mouse spleen cells; the cDNA was cloned in λgt 10 which was multiplied in *E. coli*.

Screening of this library was then carried out using the above-described human IL-2Rβ chain cDNA as the probe under non-stringent conditions. From the positive clones, a clone designated λMIL 2Rβ-26 was selected. The cDNA insert in this clone contained only a 540 bp sequence of the whole murine IL-2Rβ chain sequence. This sequence was therefore isolated by digestion of λMIL-2Rβ-26 using Pvu 2 and used for screening another cDNA library prepared using poly(A)+ from the mouse thymoma cell line EL-4 according to standard procedures and cloned into the BstXI site of the CDM8 vector followed by transfecting *E. coli*.

Screening of the cDNA library was carried out under highly stringent conditions according to the method described in European Patent Application No. 88 119 602.9 and Kashima et al. (*Nature* 313:402–404 (1985)).

Figure 7:
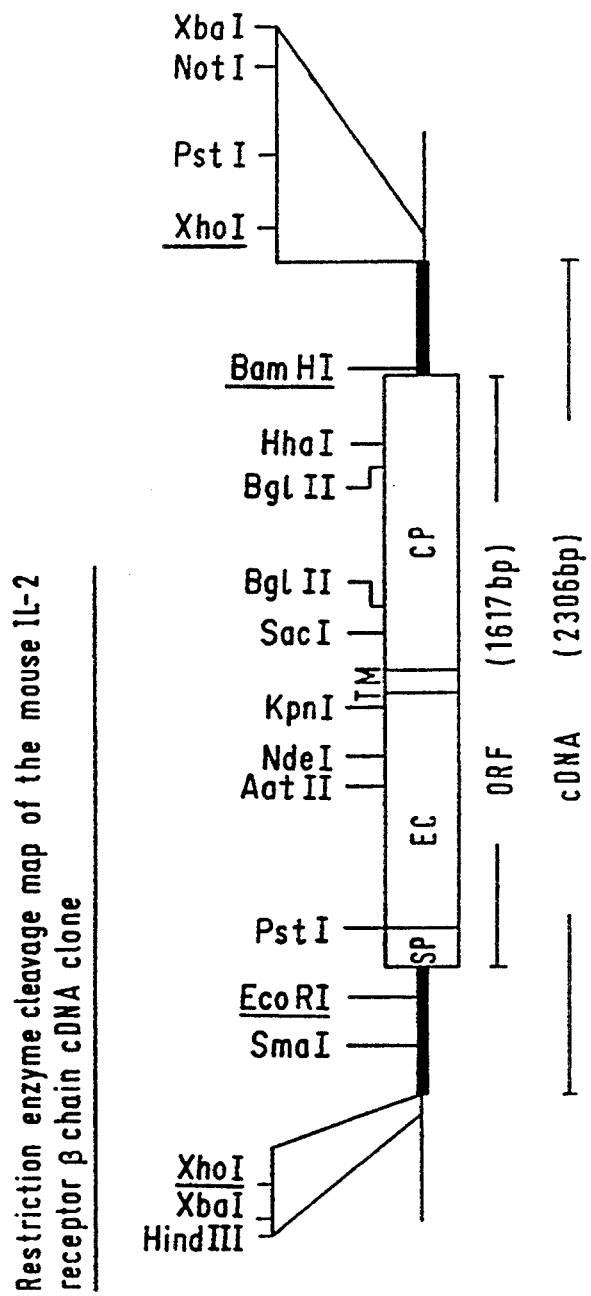
FIG. 7 shows the restriction map of the cDNA clone pMIL-2Rβ36.

From the positive clones, clone pMIL-2Rβ36 containing the structural gene for murine IL-2Rβ (see FIGS. 8A-8B) was selected. The restriction map of the cDNA clone is shown in FIG. 7.

Plasmid pMIL-2Rβ-36 has been deposited in strain *E. coli* MC 1061/P3 on May 23, 1989 at the Fermentation Research Institute according to the Budapest Treaty under accession number FERM BP-2435.

EXAMPLE 7

Preparation of Soluble Human Interleukin-2 Receptor β-chain

A secreted form of the hIL2-Rβ chain (termed hereafter soluble β) was produced by transfecting NIH 3T3 fibroblasts with the modified β-chain cDNA ("anchor minus" cDNA) lacking the entire DNA sequence encoding both intracytoplasmic and transmembrane domains of the native β-chain.

EXAMPLE 8

Construction of the Expression Vector Harboring the Anchor Minus cDNA which Encodes the Soluble β (BCMGNeo-sol.β

Figure 9:
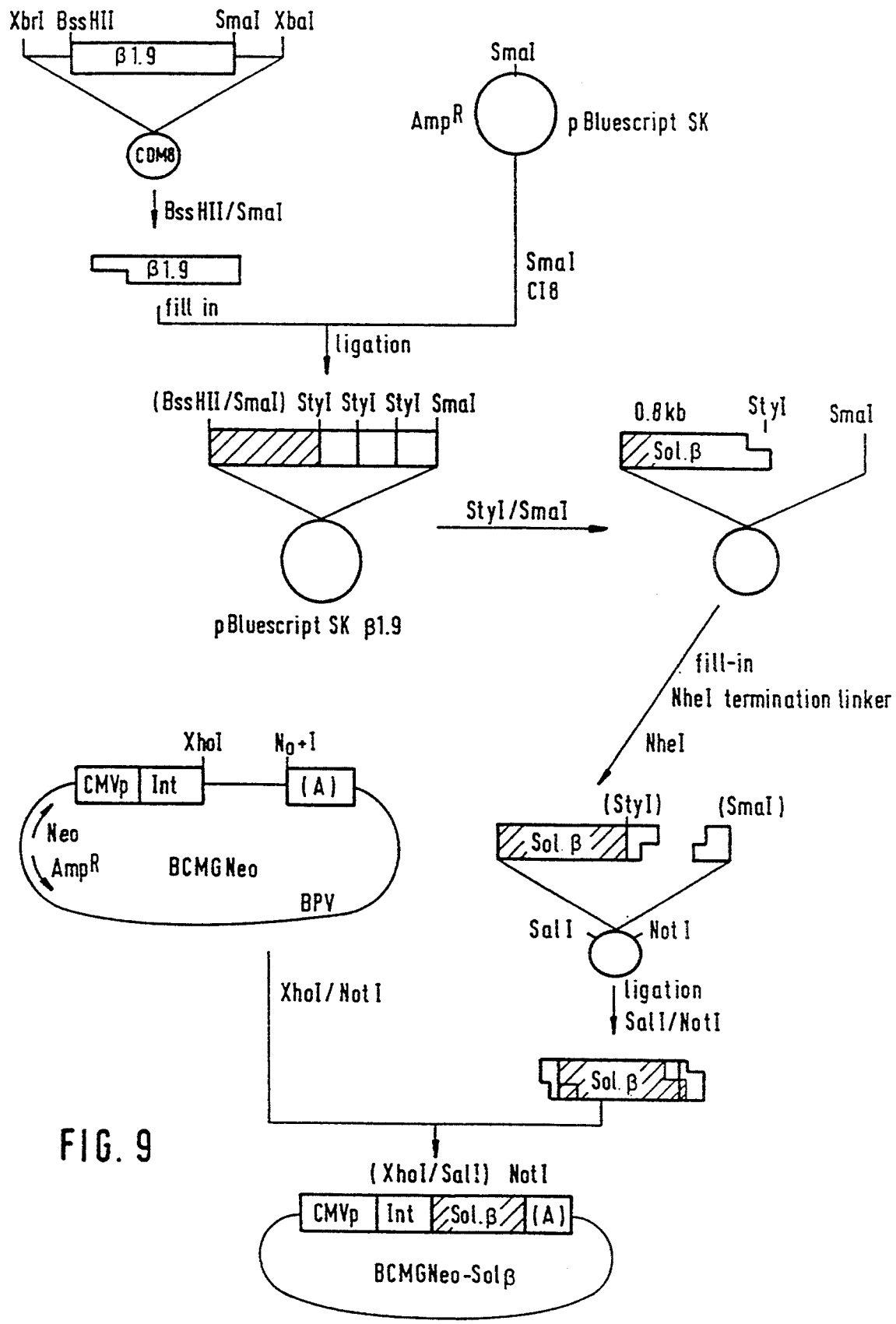
FIG. 9 depicts a strategy to generate the expression vector containing the anchor minus cDNA.

The β-chain cDNA (FIG. 1B) was modified into the anchor minus form for the production of the soluble β. A strategy to generate the expression vector containing the anchor minus cDNA is illustrated in FIG. 9. First, the plasmid pIL-2Rβ30 containing the 2.3-kb β-chain cDNA in the CDM8 vector was digested with BssH II and Sma I (all restriction enzymes were purchased from New England BioLabs, Bevery, Mass. USA), and a 1.9-kb cDNA fragment (base 58-1967) including the entire coding sequence (base 121-1773) of the β-chain was obtained. After fill-in at the BssH II end, the 1.9 kb cDNA was inserted into a SmaI restriction site of pBluescript SK vector (Strategene, San Diego, Calif., USA). This pBluescript SK-β1.9 plasmid was then digested with Sty I (restriction sites; base 825, 934 and 1235) and Sma I so that all of the intracytoplasmic and transmembrane regions were deleted, leaving bases 121-840 representing most of the extracellular region intact. Next, a 12-base synthetic linker (New England BioLabs, #1060) containing multiple termination codons (TAG) as well as the recognition sequence for Nhe I was phosphorylated and ligated to the Sty I/Sma I-digested plasmid DNA with T4 DNA ligase. After digestion with the Nhe I to remove excess linker, the DNA was ligated to the SK vector to construct pBluescript SK-sol1.β.

Figure 10B:
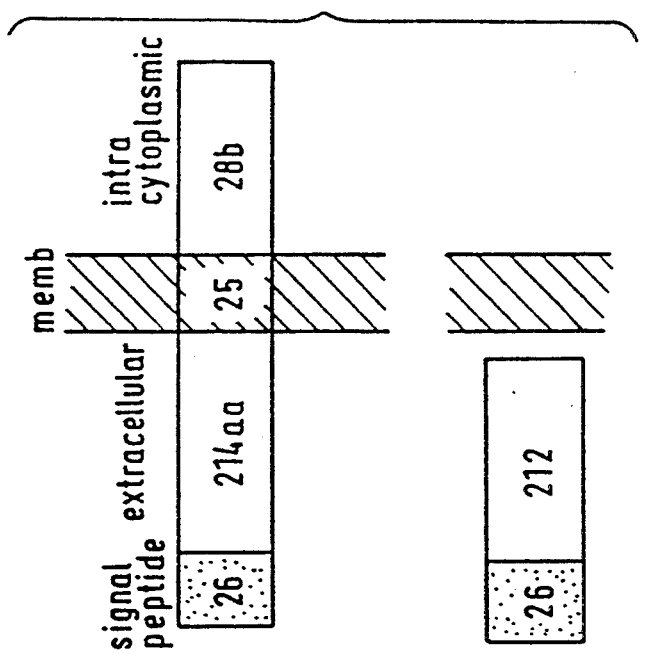
FIGS. 10A and 10B illustrate the nucleotide sequence and corresponding amino acid sequence for the native and soluble β protein.
Figure 10A:
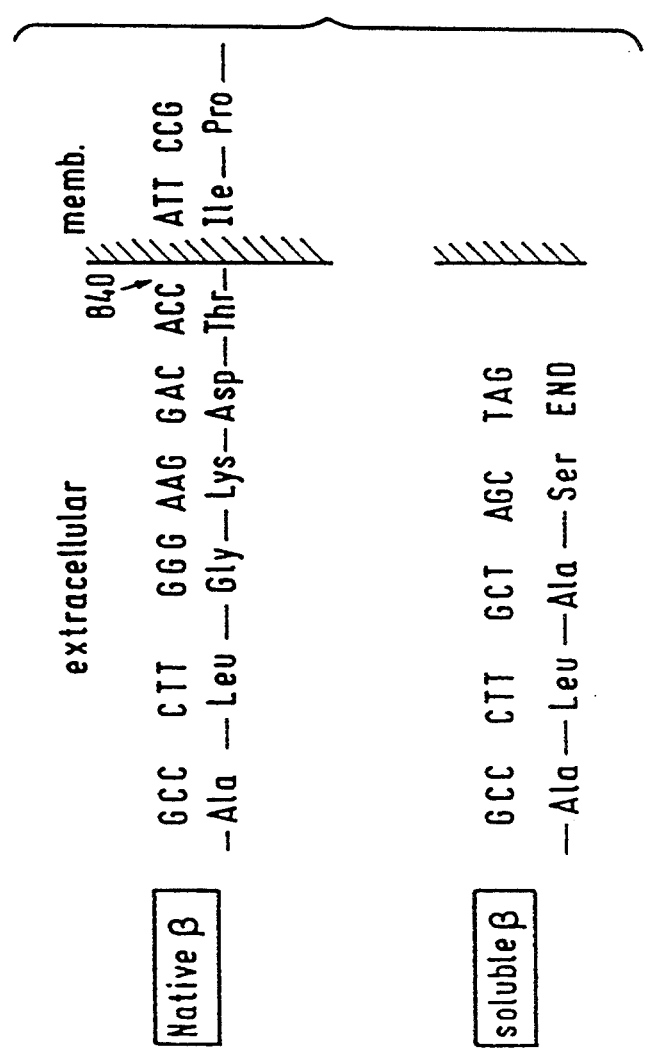

This pBluescript SK-sol.β was digested with Sal I and Not I (the restriction sites were located within the polylinker region of the pBluescript SK vector), and the resulting 0.8-kb cDNA fragment encoding the soluble β was isolated. This cDNA fragment was introduced into Xho I/Not I-digested BCMGNeo vector (see Karasuyama et al., *J. Exp. Med.* 169:13-25 (1989)) containing the cytomegalovirus (CMV) promoter and neomycin-resistance gene to generate the final expression plasmid BCMGNeo-sol.β. The BCMGNeo is a shuttle vector containing 69% of bovine papilloma virus (BPV) sequences which ensure extrachromosomal replication in mammalian cells. As illustrated in FIGS. 10A and 10B, which illustrate the nucleotide sequence and corresponding amino acid sequence for the native and soluble β, the soluble β cDNA encodes a mature protein consisting of 212 amino acids (aa) accompanied by a signal peptide of 26 aa, while the native β-chain cDNA encodes a membrane protein consisting of a signal peptide (26 aa), extracellular (214 aa), transmembrane (25 aa), and intracytoplasmic (286 aa) domains. The nucleotide and corresponding amino acid sequences for the native and soluble β are also illustrated in FIGS. 10A and 10B.

EXAMPLE 9

Transfection of NIH 3T3 Fibroblast with BCMGNeo-sol.β and Establishment of Stable Transformants Secreting the Soluble β cDNA transfection was performed by the protoplast fusion technique as described in Karasuyama et al. (supra). Briefly, bacteria containing the BCMGNeo-sol.β were converted to protoplasts and fused with a murine fibroblast cell line, NIH 3T3 by using polyethylene glycol 2,000 (Wako Chemical Industries, Osaka, Japan). Ten million protoplast-fused NIH 3T3 cells were then seeded in four 24-well plates. Twenty-five days after the culture in RPMI 1640 medium containing 10% fetal calf serum (FCS) and 750 μg/ml of G418 (Geneticin; Sigma, St. Louis, Mo., USA), transformant-cell growth was observed in 60 wells out of 104. When determined by the sandwich enzyme-linked immunosorbent assay (ELISA) as described below, culture supernatants from 18 wells out of 60 were found to be positive for the soluble β. Five clones were established by limiting dilution from a well which gave the highest absorbance in the ELISA, and they were all found to secrete high levels of soluble β (Table I). In contrast, NIH 3T3 cells transfected with the full-length β-chain cDNA (designated 3T3-β11) did not secrete the β-chain molecule to any extent. In the subsequent studies, we used the clone designated 3T3-B4-14 which secreted the highest amount of the soluble β.

TABLE 1

Levels of the soluble β in the culture supernatant of NIH 3T3 fibroblasts transfected with BCMGNeo-sol.β

| Culture supernant | Absorbance at 405 nm in ELISA |
| --- | --- |
| 3T3-B4-1 | 1.492 |
| 3T3-B4-4 | 1.301 |
| 3T3-B4-7 | 1.259 |
| 3T3-B4-14 | 1.579 |
| 3T3-B4-19 | 1.533 |
| 3T3-β11 | 0.052 |
| medium alone | 0.072 |

EXAMPLE 10

ELISA for Detecting the Soluble β

Figure 11:
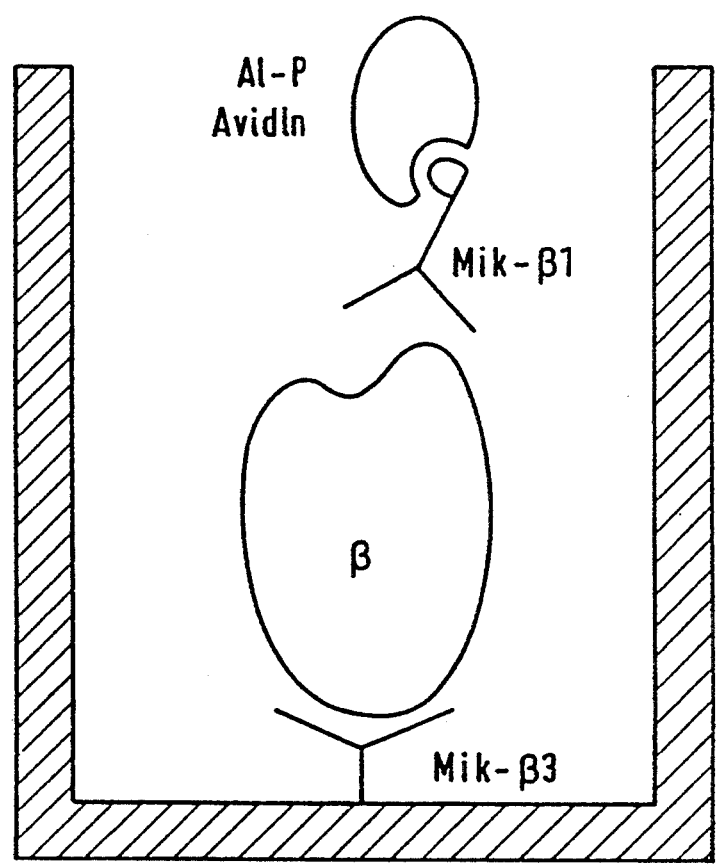
FIG. 11 is a schematic representation of the Sandwich ELISA Immulon-I microtiter plates.

Culture supernatants of transfected cells were screened for the presence of the soluble β by a sandwich enzyme-linked immunosorbent assay (ELISA). In this assay were used two monoclonal antibodies Mik-β1 and -β3, supra, and Tsudo et al., Proc. Natl. Acad. Sci. USA 86:1982–1986 (1989), which recognize the distinct epitopes on the β-chain; i.e., Mik-β1 recognizes the IL-2 binding site, while Mik-β3 recognizes the epitope not involved in the IL-2 binding. As illustrated in FIG. 11, which is a schematic representation of the Sandwich ELISA Immulon-I microtiter plates (Dynatec, Chantilly, Va., USA) were coated overnight with 50 μl of Mik-β3 at 10 μg/ml in Tris-buffered saline (10 mM Tris-HCl, pH 7.4, 0.15M NaCl). After discarding excess antibody, unbound sites were blocked by incubating with TBS containing 1% bovine serum albumin for 1 hour. After washing with TBS containing 0.05% Tween 20 (T-TBS), 50 μl of culture supernatants of the transformants were added to the wells and incubated for 1 hour. After washing, 50 μl of biotinylated Mik-β1 at 1 μg/ml were added as the secondary antibody to detect the soluble β bound to the primary antibody, Mik-β3 on the plate. After 45 minutes incubation and subsequent washing, 50 μl of alkaline phosphatase-conjugated avidin (Tago, Burlingame, Calif., USA) were added. After a 45-minute incubation, the plates were washed, 100 μl of p-nitrophenyl phosphate were added, and the abosrbance of the wells was determined at 405 nm after 45 minutes.

EXAMPLE 11

Apparent Molecular Weight of Secreted Soluble β

Figure 12:
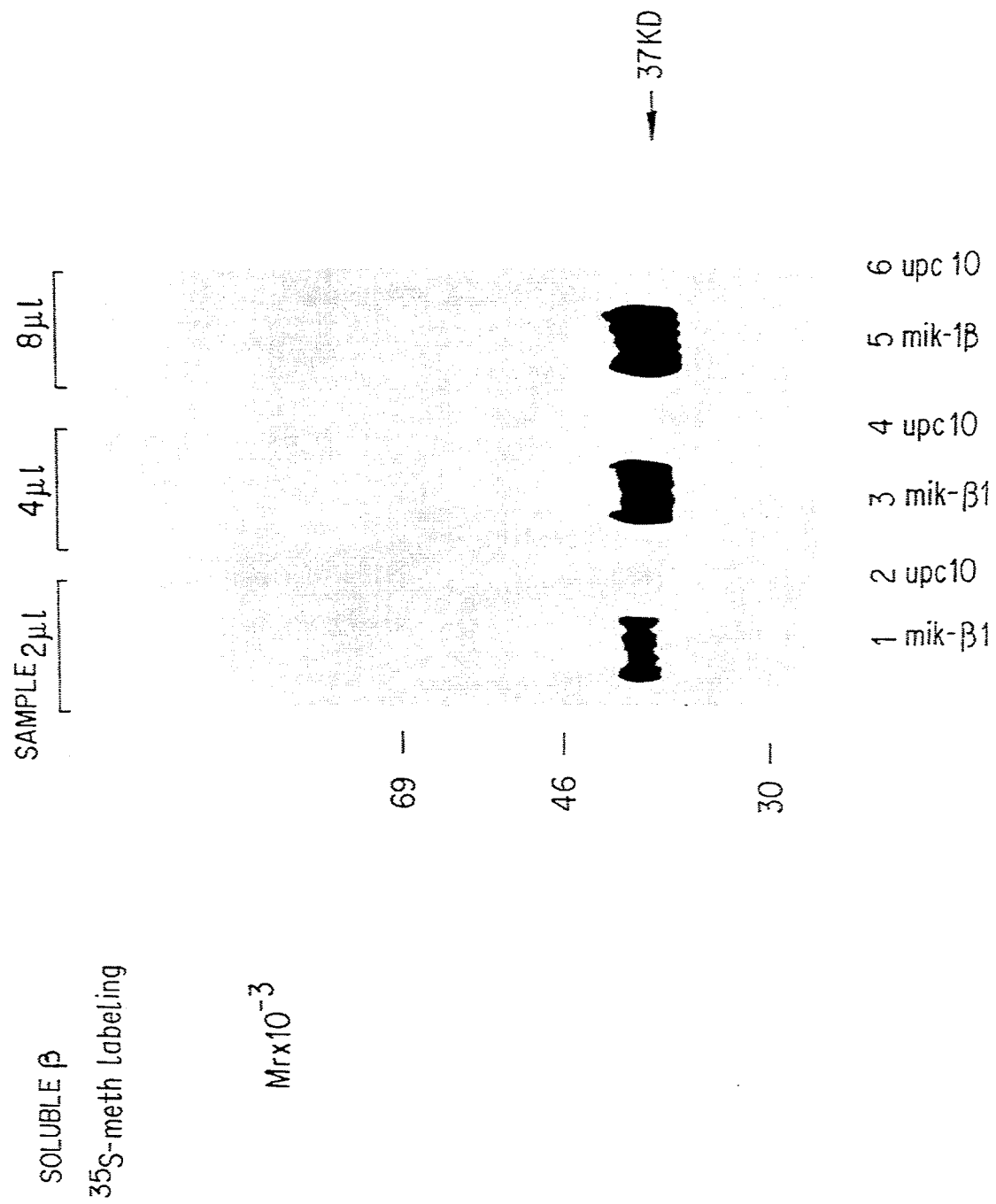
FIG. 12 depicts SDS-polyacrylamide gel electrophoresis (PAGE) of various amounts of immunoprecipitates using the Mik-β1 and, as control UPC 10 mAb, with the culture supernatant of biosynthetically labeled 3T3-B4-14 cells.

In order to define the molecular size of the soluble β, the 3T3-B4-14 cells were biosynthetically labeled with $^{35}$S-methionine, and the soluble β immunoprecipitated by the Mik-β1 mAb from the culture supernatant. Various amounts of immunoprecipitates using the Mik-β1 and, as control UPC 10 mAb for precipitation were loaded and electrophoresed on an 8% SDS-polyacrylamide gel. As shown in FIG. 12, when examined by the SDS-polyacrylamide gel electrophoresis (PAGE), the Mik-β1, but not the control UPC 10 mAb, identified a single species of protein with an apparent Mr of 37,000 in the culture supernatant of 3T3-B4-14 cells. This molecular size is in good agreement with that predicted for the truncated β-chain lacking all the transmembrane (25 aa) and intracytoplasmic (286 aa) regions.

EXAMPLE 12

IL-2 Binding Ability of the Soluble β

Figure 13A:
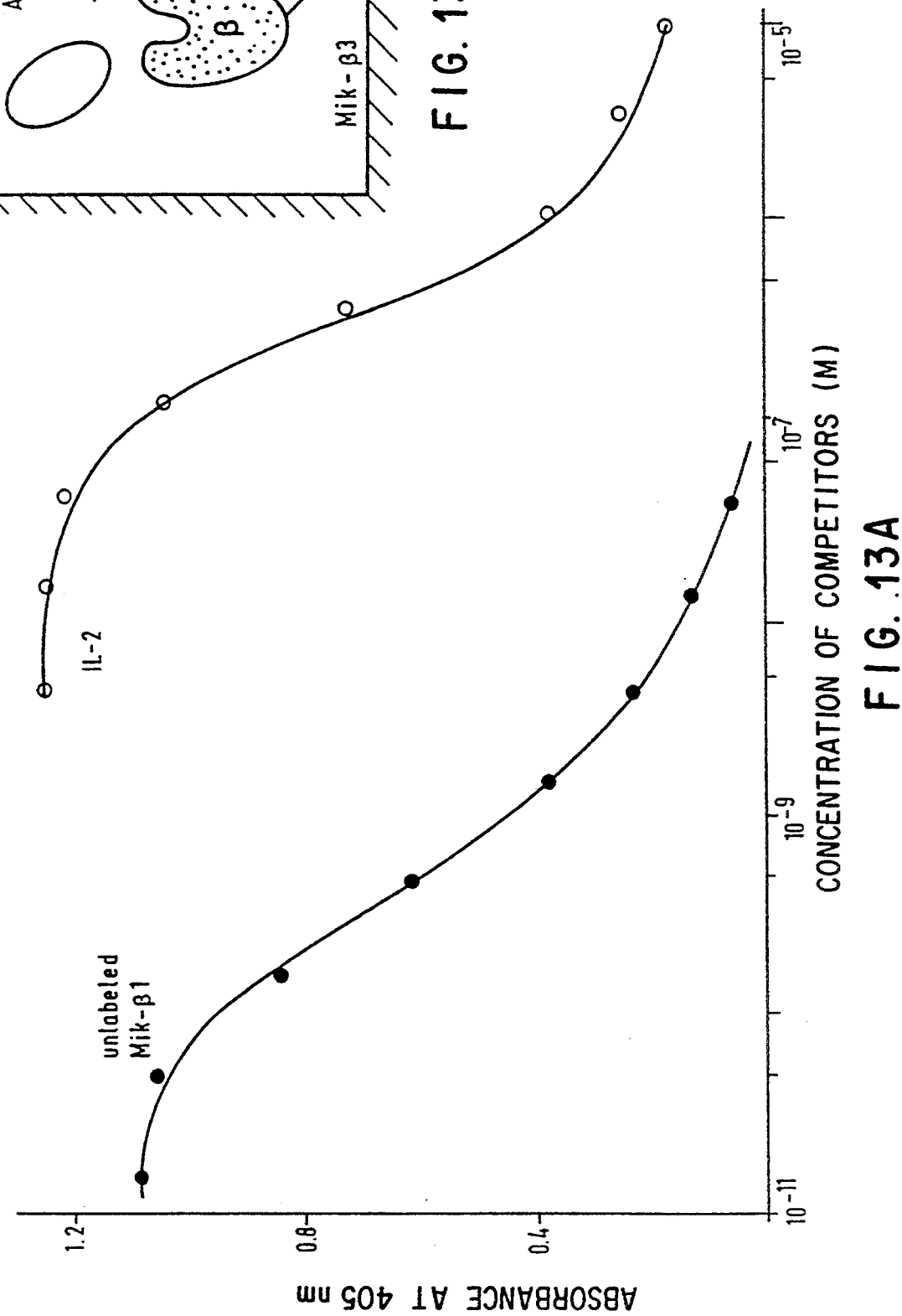
FIGS. 13A and 13B show the results of a competitive sandwich ELISA.
Figure 13B:
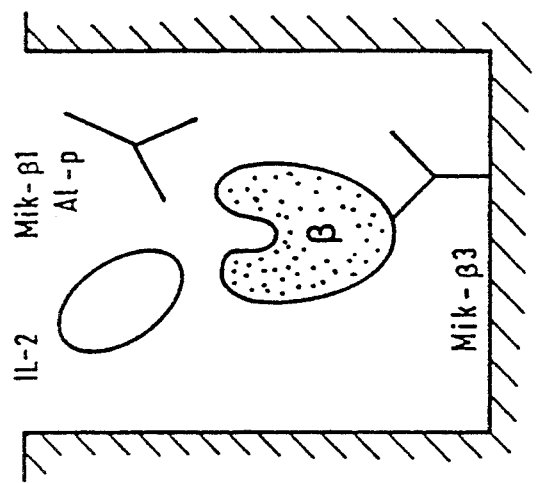

It was then investigated whether the secreted form of the β-chain is capable of binding IL-2. To this end, a "competitive" sandwich ELISA was employed. In this assay, the soluble β in the culture supernatant was fixed on the solid phase by the Mik-β3 mAb, a non-inhibitory mAb for IL-2 binding, so that the putative IL-2 binding site on the β-chain would remain unoccupied. Then, serial dilutions of IL-2 or unlabeled Mik-β1 were added as competitors for biotinylated Mik-β1. FIG. 13A shows the results of the competitive sandwich ELISA in which the curve -●-●- is for serial dilutions with unlabeled Mik-β1 and -o-o- for serial dilutions of IL-2. As shown in FIG. 13A unlabeled Mik-β1 reduced the absorbance dose-dependently, showing the specificity of this system. Likewise, IL-2 efficiently competed dose-dependently with biotinylated Mik-β1 for the binding to the soluble β, indicating that the soluble β is indeed capable of binding IL-2.

This competition curve is quite similar to that found for the detergent-solubilized native β-chain from YTS cells which express the β-chain alone, indicating that the affinity of the soluble β to IL-2 is comparable to that of the solubilized native β-chain.

The availability of the genes encoding IL-2Rβ chains makes it possible to explore novel approaches for the functional studies of the IL-2 system. The receptor structure operating in the IL-2 system is unique in that two structurally distinct membrane molecules, the IL-2Rα and IL-2Rβ chains, both bind IL-2 independently. The series of cDNA expression examples described herein substantiate further the previous notion-that the α and β chains constitute the high-affinity IL-2R complex via a non-covalent association of the molecules (Hatakeyama, M., et al., *J. Exp. Med.* 166:362 (1987); Kondo, S., et al., *Nature* 327:64 (1987); Potter, H., et al., *Proc. Natl. Acad. Sci. USA* 81:7161 (1984)). Thus, the peculiarity of this system is the involvement of three intermolecular interactions between one ligand and two distinct receptors. By virtue of the present invention it will now be possible to elucidate functional domains of this unique cytokine receptor system. Mutational analyses of the cloned β chain cDNA may provide clues as to the identification of respective domains involved in ligand binding and association with the α chain. To date, little is known about the cascade of biochemical events triggered by cytokines interacting with their homologous receptors. By the present invention we have demonstrated the presence in the IL-2Rβ chain of a large cytoplasmic region which most likely is involved in driving the IL-2 signal pathway(s). The particular acidic nuclei found in the cytoplasmic region may suggest coupling to other cytoplasmic signal transducers. Alternatively, in view of a previous report on the presence of IL-2 within the nucleus (Robb, R. J., et al., *J. Exp. Med.* 165:1201 (1987)), an intriguing possibility is tha the acidic as well as the proline-rich regions of the IL-2Rβ cytoplasmic component may play a role in activation of the genetic programming. The availability of the expression system in which the cDNA-encoded β chain can deliver growth signals will allow further clarification of the functional domains of the receptor. It is now possible to study the essential role of IL-2 in the development and regulation of the immune system.

The availability of soluble counterparts to the cell surface receptor β-chain should facilitate structural analysis of the β-chain since crystallization of soluble molecules is more easily accomplished than insoluble ones. The soluble molecules can also be used to neutralize the actual cell surface receptors for studies of the biological functions of the receptors or for therapeutic purposes.

We claim:

1. A substantially pure protein fragment of IL-2Rβ which is soluble in aqueous solution and capable of binding specifically to IL-2, wherein said protein fragment lacks the transmembrane and intracytoplasmic regions of said IL-2Rβ, and comprises the amino acid sequence beginning with any one of amino acids 1–10 terminating with any one of amino acids 200–220 of FIG. 1B.

* * * * *